US010071053B2

(12) United States Patent
Victor et al.

(10) Patent No.: US 10,071,053 B2
(45) Date of Patent: Sep. 11, 2018

(54) TEA COMPOSITION FOR ORAL ADMINISTRATION

(71) Applicant: Pocket Tea, LLC, New York, NY (US)

(72) Inventors: Daniel Victor, New York, NY (US); Melissa Flagg, Chicago, IL (US); Peter Maletto, Point Pleasant Beach, NJ (US)

(73) Assignee: Pocket Tea, LLC, New York, NY (US)

( * ) Notice: Subject to any disclaimer, the term of this patent is extended or adjusted under 35 U.S.C. 154(b) by 281 days.

(21) Appl. No.: 15/100,288

(22) PCT Filed: Jan. 30, 2015

(86) PCT No.: PCT/US2015/013927
§ 371 (c)(1),
(2) Date: May 27, 2016

(87) PCT Pub. No.: WO2015/117011
PCT Pub. Date: Aug. 6, 2015

(65) Prior Publication Data
US 2016/0324777 A1 Nov. 10, 2016

Related U.S. Application Data

(60) Provisional application No. 61/965,474, filed on Jan. 31, 2014.

(51) Int. Cl.
| | |
|---|---|
| A61K 36/00 | (2006.01) |
| A61K 9/00 | (2006.01) |
| A23F 3/14 | (2006.01) |
| A23F 3/34 | (2006.01) |
| A23F 3/40 | (2006.01) |
| A61K 36/82 | (2006.01) |
| A61K 36/484 | (2006.01) |
| A61K 36/752 | (2006.01) |
| A61K 31/522 | (2006.01) |
| A61K 35/644 | (2015.01) |
| A61K 36/185 | (2006.01) |
| A61K 36/28 | (2006.01) |
| A61K 36/62 | (2006.01) |
| A23L 29/00 | (2016.01) |
| A23L 27/10 | (2016.01) |
| A23L 27/14 | (2016.01) |
| A23L 27/20 | (2016.01) |
| A23L 27/30 | (2016.01) |
| A23L 33/105 | (2016.01) |
| A23L 33/175 | (2016.01) |
| A23L 33/26 | (2016.01) |
| A61K 31/198 | (2006.01) |
| A61K 31/352 | (2006.01) |
| A61K 31/4045 | (2006.01) |
| A61K 36/23 | (2006.01) |
| A61K 36/258 | (2006.01) |
| A61K 36/31 | (2006.01) |
| A61K 36/35 | (2006.01) |
| A61K 36/42 | (2006.01) |
| A61K 36/534 | (2006.01) |
| A61K 36/539 | (2006.01) |

(Continued)

(52) U.S. Cl.
CPC .............. *A61K 9/0095* (2013.01); *A23F 3/14* (2013.01); *A23F 3/34* (2013.01); *A23F 3/405* (2013.01); *A23L 27/10* (2016.08); *A23L 27/14* (2016.08); *A23L 27/20* (2016.08); *A23L 27/36* (2016.08); *A23L 29/015* (2016.08); *A23L 29/035* (2016.08); *A23L 33/105* (2016.08); *A23L 33/175* (2016.08); *A23L 33/26* (2016.08); *A61K 9/0053* (2013.01); *A61K 31/198* (2013.01); *A61K 31/352* (2013.01); *A61K 31/4045* (2013.01); *A61K 31/522* (2013.01); *A61K 35/644* (2013.01); *A61K 36/185* (2013.01); *A61K 36/23* (2013.01); *A61K 36/258* (2013.01); *A61K 36/28* (2013.01); *A61K 36/31* (2013.01); *A61K 36/35* (2013.01); *A61K 36/42* (2013.01); *A61K 36/484* (2013.01); *A61K 36/534* (2013.01); *A61K 36/539* (2013.01); *A61K 36/62* (2013.01); *A61K 36/67* (2013.01); *A61K 36/752* (2013.01); *A61K 36/82* (2013.01); *A61K 36/9068* (2013.01); *A61K 47/02* (2013.01); *A61K 47/10* (2013.01); *A61K 47/36* (2013.01); *A23V 2002/00* (2013.01)

(58) Field of Classification Search
CPC ..................................................... A61K 36/00
USPC .......................................................... 424/725
See application file for complete search history.

(56) References Cited

U.S. PATENT DOCUMENTS 7,214,399 B2  5/2007  Froehlich et al.
7,874,297 B2  1/2011  Streck
(Continued)

FOREIGN PATENT DOCUMENTS

CN        101874523 A    11/2010
WO    2007126361 A1    11/2007

OTHER PUBLICATIONS

International Searching Authority, International Search Report for PCT/US15/13927, dated Apr. 23, 2015.
(Continued)

Primary Examiner — Michael V Meller
(74) Attorney, Agent, or Firm — Wright IP & International Law; Eric G. Wright

(57) ABSTRACT

This invention concerns an enhanced green tea based product for oral use whereby the nutritional and health benefits of green tea, and additives which shall include some combination of flavoring, preservatives, caffeine, humectants, and water, can be ingested and absorbed by the user.

4 Claims, 12 Drawing Sheets

(51) Int. Cl.
    *A61K 36/67*       (2006.01)
    *A61K 36/9068*     (2006.01)
    *A61K 47/02*       (2006.01)
    *A61K 47/10*       (2017.01)
    *A61K 47/36*       (2006.01)

(56) References Cited

U.S. PATENT DOCUMENTS

| | | |
|---|---|---|
| 8,172,378 B2 | 5/2012 | Cai |
| 2005/0152997 A1 | 7/2005 | Selzer et al. |
| 2005/0181044 A1* | 8/2005 | Romero .................. A23F 5/385 |
| | | 424/464 |
| 2007/0292560 A1 | 12/2007 | Quan et al. |
| 2010/0233322 A1 | 9/2010 | Fukauda et al. |

OTHER PUBLICATIONS

BadKittySmiles, Grasscity.com Grasscity forums; medical smoking and usage; tokers Q and A; badkitysmiles post Apr. 28, 2012. pp. 1-14 (retreived on Apr. 9, 2015). Retrieved from the internet;<URL: http://forum.grasscity.com/tokers-qa/1039445-can-you-use-weed-dip.html> p. 3, fifth paragraph.

BrewMaryJane, Grasscity forums; medical smoking and usage; incredible, edible herb; brewmaryjane post. Jan. 18, 2011. pp. 1-18 (retreived on Apr. 9, 2015) Retrieved from the internet; <URL: http://forum.grasscity.com/incredible-edible-herb/734531-brew-weed-tea-w-bicutresquick-tasty.html> p. 1, brewmaryjane.

Ask Metafilter a weigh-tea-matter. Aug. 18, 2009. (retreived on Apr. 9, 2015). Retreived from the internet; <URL: http://ask.metafilter.com/130564/A-weightea-matter> p. 2, third and fourth paragraphs.

\* cited by examiner

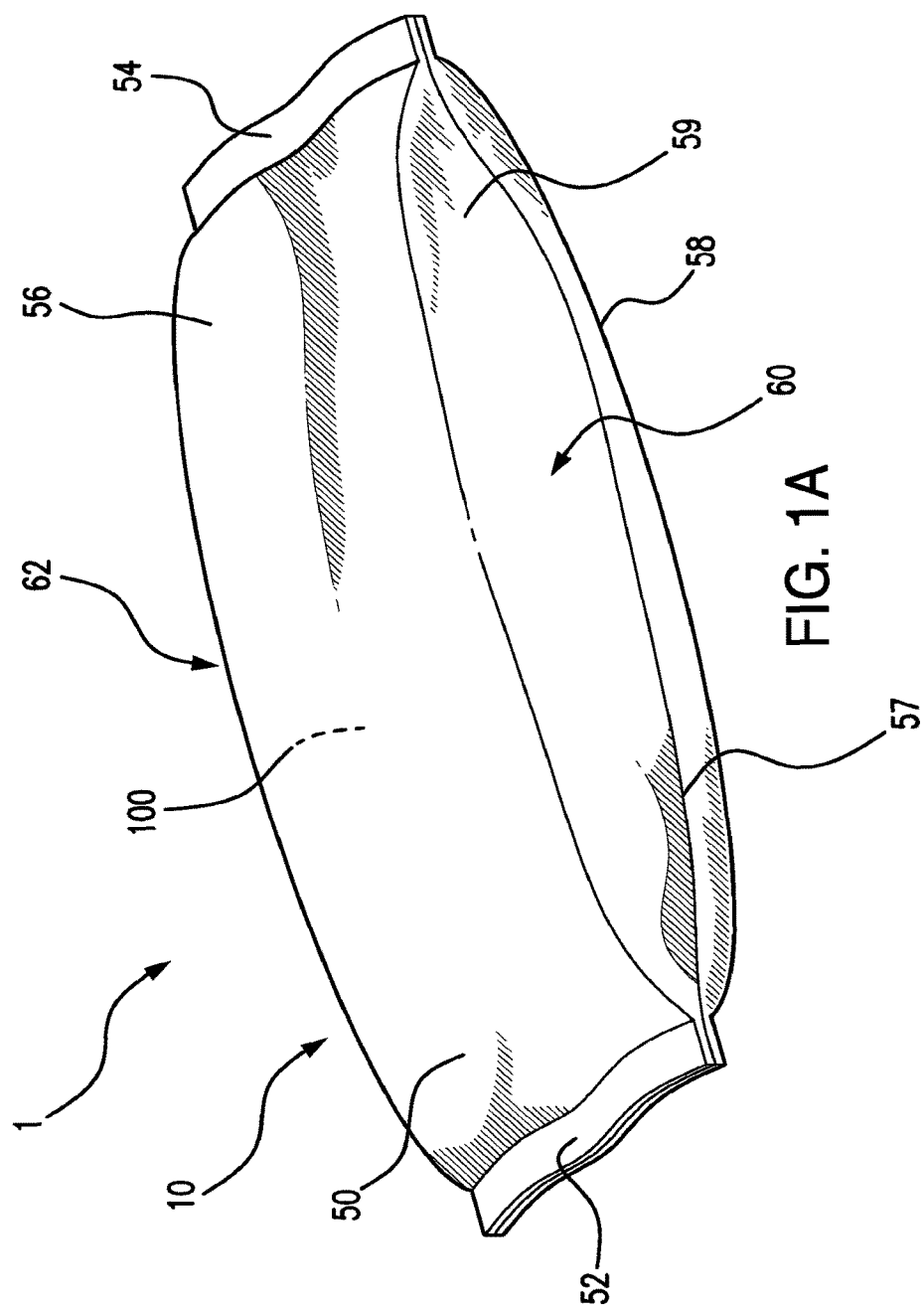

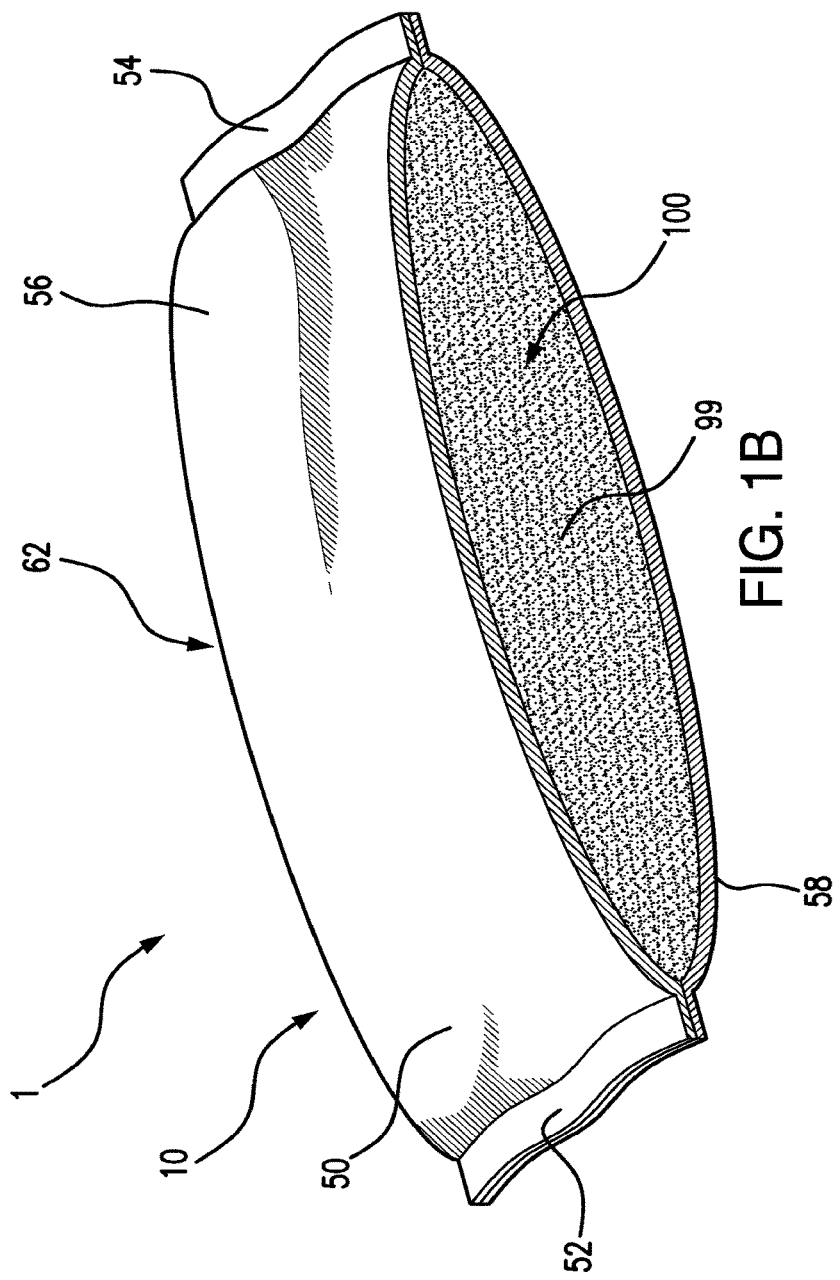

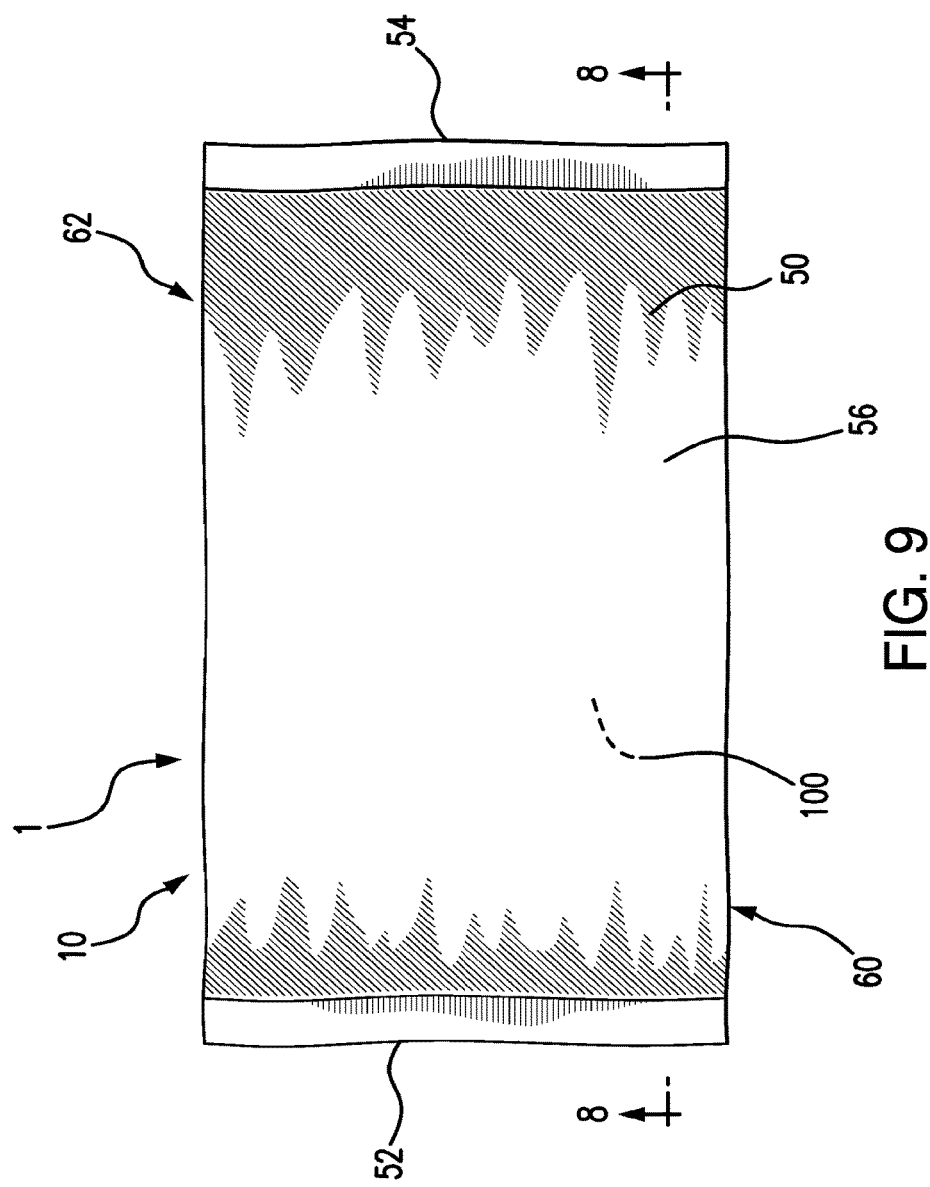

TEA COMPOSITION FOR ORAL ADMINISTRATION

CROSS-REFERENCE TO RELATED APPLICATIONS

This patent application is a Patent Cooperation Treaty application of and claims the benefit of the filing date of U.S. provisional patent application No. 61/965,474 entitled "Tea Composition For Oral Administration" filed on Jan. 31, 2014.

This patent application is a non-provisional application of and claims the benefit of the filing date of U.S. provisional patent application No. 61/965,474 entitled "Tea Composition For Oral Administration" filed on Jan. 31, 2014.

FIELD OF THE INVENTION

Tea Products

INCORPORATION BY REFERENCE

This patent application incorporates by reference in its entirety U.S. provisional patent application No. 61/965,474 entitled "Tea Composition For Oral Administration" filed on Jan. 31, 2014, and having confirmation number 7882.

BACKGROUND OF THE INVENTION

Energy products are typically unhealthy and poor tasting. Additionally, such products require the user to drink them like a liquid, swallow them as a pill or to eat them as a food product.

In the area of teas, most enjoyment and benefits of tea requires time consuming preparation, or the ingestion of a pill. A convenient method for the enjoyment and benefits of tea over a period of time, without the traditional brewing process is lacking and strongly needed.

Additionally, there is a strong need for a product having tea which can be enjoyed over time, is organic and healthy for the user, does not require refrigeration, and is not readily susceptible to the growth of mold and unhealthy bacteria. Thus, a shelf-stable product is needed that can provide a user with flavors and health benefits lacking in the market of energy products.

SUMMARY OF THE INVENTION

Green tea compositions can be used and consumed in a variety of ways most commonly in a dried form in a porous bag which is infused with water to create a tea drink. As disclosed herein, green tea extract is also commonly used as an additive in beverages and other products designed for ingestion. The health benefits of the green tea compositions disclosed herein can include, but are not limited to, weight loss, diabetes, heart disease, esophageal cancer, cholesterol, Alzheimer's, Parkinson's, tooth decay, blood pressure, depression, skin care, malodorous breath, provides antioxidants, caffeine, increased metabolism, prevent arthritis, minimize allergies, quitting smoking, pleasure in tasting, pleasure in ingesting, pleasure in chewing, pleasure in sucking on, as well as many others.

In addition to its ordinary and customary meaning, herein the word "composition" is used synonymously with "tea composition" when regarding ingredients, constituents, materials or attributes of a composition having any type of tea, tea extract, tea derivative or tea flavor as a component.

In addition to its ordinary and customary meaning, "composition" is used herein synonymously with the term "formulation" and/or "formula" when regarding ingredients, constituents, materials or attributes of a composition having any type of tea, tea extract, tea derivative or tea flavor as a component. Additionally, a "tea composition" can be any one or more of a yerba mate base tea composition, a chamomile base tea composition, a marijuana base tea composition, a *Cannabis* base tea composition, or tea base tea composition, or other base tea composition; which herein are all examples of tea compositions and/or compositions.

In an embodiment, a green tea based formulation can comprise and/or have one or more of the following constituents: green tea leaves and/or flowers and/or stems and/or seeds and/or roots; a stimulant and/or caffeine; one or more humectants; NaCl; water; and additional plant material and/or cellulose.

In an embodiment, the composition can have plant material and/or plant material constituents in any one or more of the following forms: Leaves, flowers, stems, seeds, roots, grindings, pieces, powder, mass from and extracts. Optionally, the plant material can be dried and/or ground.

The composition can have plant material from any of the plants or parts of plants disclosed herein. The plant material can be harvested, cut from, taken from, part of, or extracted from any of the plants disclosed herein. The composition can also have seeds and/or other matter derived or from any of the plants disclosed herein. For example, the composition can contain extracts, powders, oils, juices, flavonoids, metabolites and other derivatives of any of the materials disclosed herein.

The composition can also have cellulose, as well as other, fiber fibrous and/or bulk plant materials.

The tea composition can have any one or more of the following ingredients: tea, green tea, white tea, yellow tea, oolong, black tea, *Stevia, Glycyrrhiza* root (licorice root), *Camellia sinensis, Camellia sinensis* var. *sinensis* and/or *Camellia sinensis* var. *assamica* (tea), yerba mate (*Ilex paraguariensis*), peppermint (*Mentha×piperita*), and/or *Cannabis sativa* (marijuana).

The tea composition can have a stimulant which can be any one or more of the following: caffeine, nicotine, coffee, tobacco, gotu kola extract, gotu kola root, kola nut, cocoa, guarana, yerba mate, yerba mate extract, L-theanine, huperzine serrate and maca extract. In embodiments the tea composition can be free of any stimulant or stimulants. For example, the tea composition can be nicotine-free and can have no nicotine or essentially no nicotine. In another example, the tea composition can be tobacco-free and can have no tobacco or essentially no tobacco.

The tea composition can have a humectant. The tea composition can have one or more of the following humectants: Zemea® (also known as USP-FCC 1, 3 propanediol; from DuPont Tate & Lyle BioProducts, 198 Blair Bend Drive, Louden, Tenn. 37774, (866) 404-7933), glycerol, sorbitol, polydextrose and propylene glycol.

The tea composition can have an herbal extract and/or an antioxidant. In an embodiment an herbal extract such as a milk thistle extract can be used. The milk thistle extract can also be used as an antioxidant.

The tea composition can have one or more of the following inorganic compounds NaCl and Water.

The tea composition can have one or more of the following natural flavorants: ginseng, rose hips, pomegranate, acai berry, grape seed, lemon, lemon peel, lemon juice powder, cranberry, mint, cinnamon, green tea, coffee bean, mint, spearmint (*Mentha spicata*), wintergreen (*Gaultheria*

*procumbens*), peppermint (*Mentha×piperita*), rosemary, passion flower, *Glycyrrhiza* root (licorice root), cocoa, ginger and bee pollen.

The tea composition can have one or more extracts from any one or more of the following: ginseng, rose hips, pomegranate, acai berry, grape seed, lemon, lemon peel, cranberry, mint, cinnamon, green tea, coffee bean, mint, spearmint (*Mentha spicata*), wintergreen (*Gaulthcria procumbens*), peppermint (*Mentha×piperita*), rosemary, passion flower, *Glycyrrhiza* root (licorice root), cocoa, ginger and bee pollen.

The tea composition can have any one or more of the following flavors a grape flavor, a lemon flavor, a citrus flavor, a wintergreen flavor, a spearmint flavor, a peppermint flavor, a coffee flavor, a cocoa flavor, a pomegranate flavor, an acai berry flavor, a cinnamon flavor, a cranberry flavor, a ginseng flavor, a rose hips flavor, a rosemary flavor, a passion fruit flavor, a licorice flavor, a ginger flavor, a honey flavor, tartaric, malic acid, and citric acid. Any flavor disclosed herein can be natural or artificial.

In an embodiment, the tea composition can have a lemon balm (*Melissa officinalis*) and/or a lemon juice powder. The lemon balm can be used to provide a calming and sedative effect to the user.

Optionally, the tea composition can have one or more natural or artificial colorants. Optionally, the tea composition can be colorant free.

The tea composition can have plant material harvested from *Cannabis sativa*. The tea composition can have tetrahydrocannabinol (THC). The THC can be in a natural state, as an extract, processed and/or modified from its natural form. In an embodiment, the tea composition can have cannabidiol (CBD).

The tea composition can have a sweetener such as any one or more of the following a *Stevia*, an agave, monk fruit extract, honey and honey powder.

The tea composition can have Propolis.

In another embodiment PUREFRUIT™ product and/or PUREFRUIT™ Select and/or any PUREFRUIT™ or equivalent product can be used in the tea composition as a sweetener. In an embodiment, the tea composition can comprise monk fruit and/or a monk fruit derivative, extract, oil, material or powder. PUREFRUIT™ is a monk fruit extract product line produced by Tate & Lyle PLC, 1 Kingsway, London, WC2B 6AT, UK, 44 (0)20 7257 2100. Any PUREFRUIT™ product can optionally be used in the tea compositions disclosed herein. In an embodiment PUREFRUIT™ Select can be used. In an embodiment, PUREFRUIT™ Select (also labeled as Monk Fruit Extract) can be a white to light yellow powder and can have the following non-limiting specification: mogroside v 48-52%, particle size ≥95% pass mesh 80, moisture ≤6.0%, ash ≤5.0%, arsenic ≤0.5 ppm, cadmium <1 ppm, lead ≤1 ppm, total bacteria count 5,000 max/gram, yeasts & mold 100 max/gram, coliforms 10 max/gram, *e. coli* negative, and *salmonella* negative. Equivalents and substitutes for any PUREFRUIT™ product and/or PUREFRUIT™ Select can be used in the compositions disclosed herein.

The tea composition can have one or more of the following sedatives: kava (*Piper methysticum*), chamomile, melatonin, valerian (*Valeriana officinalis*), valerian root, skullcap (genus *Scutellaria*), and lemon balm (*Melissa officinalis*).

The tea composition can have extracts of one or more of the following sedatives: kava (*Piper methysticum*), chamomile, melatonin, valerian (*Valeriana officinalis*), valerian root, skullcap (genus *Scutellaria*), and lemon balm (*Melissa officinalis*).

The tea composition can have any one or more of the following additives: guar gum, huperzine serrate, maca extract, L-theanine, caffeine powder, caffeine liquid, sodium gluconate and lemon juice powder.

The tea composition can have an oil, such as but not limited to hemp oil or flax seed oil. The tea composition can also have one or more of: a flavored oil, a naturally derived oil, a natural oil, and an ingestible oil.

The tea composition can have *Stevia rebaudiana* and/or a rebaudioside (a steviol glycoside, e.g. rebaudioside A-E).

Numeric values and ranges herein, unless otherwise stated, also are intended to have associated with them a tolerance and to account for variances of design and manufacturing. Thus, a number can include values "about" that number. For example, a value X is also intended to be understood as "about X". Likewise, a range of Y-Z, is also intended to be understood as within a range of from "about Y-about Z". Unless otherwise stated, significant digits disclosed for a number are not intended to make the number an exact limiting value. Variance and tolerance is inherent in formulations, compositions, chemistry, testing, measurement and standards, as well as mechanical designs and the numbers disclosed herein are intended to be construed to allow for such factors (in non-limiting e.g., ±10 percent of a given value). Likewise, the claims are to be broadly construed in their recitations of numbers and ranges.

Herein ranges can be disclosed by a variety of recitations, for non-limiting example as X-Y %, or X %-Y %, or X to Y %, or X % to Y %, or other recitation.

Unless otherwise disclosed, a percentage of a material of a tea composition disclosed herein is a weight percent (wt %).

The amount of water present in the tea composition can be selected from over a broad range, for example from desiccated and/or bone dry, such as less than 0.025 wt %, to approximately 20 wt %, or higher. In an embodiment, the water in the tea composition can range from 0.025 wt % to 10 wt %, such as from 0.05 wt % to 8 wt %, 0.05 wt % to 8 wt %, 0.05 wt % to 6 wt %, 0.05 wt % to 5 wt %, 0.05 wt % to 4 wt %, 0.05 wt % to 3 wt %, 0.05 wt % to 2 wt %, 0.05 wt % to 1 wt %, 1.0 wt % to 6 wt %, 1.0 wt % to 5 wt %, 1.0 wt % to 4 wt %, 1.0 wt % to 3 wt %, or 1.0 wt % to 2 wt %. In another embodiment, the water in the tea composition can be in non-limiting example less than 10 wt %, less than 5 wt %, less than 4 wt %, less than 3 wt %, less than 2 wt %, less than 1 wt %, or less than 0.05 wt %.

In an example embodiment, the tea composition can have: 30 wt % or less plant material harvested from *Camellia sinensis*; yerba mate in a concentration of 40 wt % or less; peppermint leaf or leaf powder in a concentration of 20 wt % or less; lemon juice powder in a concentration of 40 wt % or less; and honey powder in a concentration of 40 wt % or less.

In an embodiment, the water of the tea composition can be the naturally occurring moisture of the constituents of the tea composition. In another embodiment, the water can be a concentration of water which is retained in dried or desiccated constituents of the tea composition.

In another embodiment, the water can be in addition to the water of the ingredient materials of the tea composition. The water can also be a combined amount of water of the ingredient materials of the tea composition and water added to the tea composition.

In another embodiment, humectants can also contribute an amount of water to the tea composition.

In an embodiment, the tea composition can have sodium gluconate which can inhibit bitterness.

In an embodiment, the tea composition can have yerba mate and/or any one or more of yerba mate leaf, powder, extract, oil, flavor, or flavonoid.

In an embodiment, the tea composition can have peppermint leaf and/or any one or more of peppermint powder, extract, oil, flavor, or flavonoid. A "peppermint" as used herein can be any one or more of peppermint leaf, peppermint extract, peppermint leaf powder (also as peppermint powder), peppermint powder from other source, peppermint oil, peppermint flavor, or peppermint flavonoid. A "peppermint" can also be any peppermint flavor. Herein, any flavor can be a natural flavor or a synthetic flavor. For example, peppermint and/or a peppermint flavor can also be a natural peppermint flavor or an artificial peppermint flavor.

For any flavor disclosed herein, that flavor can be derived in the composition by use of a plant material, powder, extract, oil, flavor or flavonoid. As for general non-limiting example, a peppermint as used herein can be any one or more of peppermint leaf, peppermint extract, peppermint leaf powder, peppermint oil, peppermint flavor, or peppermint flavonoid.

In an embodiment, the tea composition can have green tea extract and/or any one or more of green tea leaves, powder, oil, flavor, flavonoid, or antioxidant.

In an embodiment, the tea composition can have green tea loose leaf and/or any one or more of green tea, green tea leaf, green tea plant material, green tea powder, cut green tea, chopped or shredded green tea, processed green tea, green tea extract, oil, flavor, flavonoid, or antioxidant.

In an embodiment, the tea composition can have Lemon juice powder and/or any one or more of lemon flavor, citrus flavor, lemon oil, citrus oil, or other flavor or oil.

In an embodiment, L-theanine can be added in a range of from 0.15 wt % to 25 wt % to provide or assist the user with mental Focus.

In an embodiment, huperzine serrate can be added in a range of from 0.01 wt % to 10 wt %, or 0.05 wt % to 3 wt %, or 0.05 wt % to 1 wt %, to provide or assist the user with mental focus.

In an embodiment, maca extract can be added in a range of from 0.1 wt % to 10 wt % to provide or assist the user with vitality.

In an embodiment, chamomile can be added in a range of from 0.5 wt % to 35 wt %, or 3 wt % to 60 wt %, to provide or assist the user with relaxation. In an embodiment, kava (*Piper methysticum*) can be added in a range of from 0.5 wt % to 35 wt % to provide or assist the user with relaxation.

In an embodiment, melatonin can be added in a range of from 0.05 wt % to 0.5 wt % to provide or assist the user with sleep.

In an embodiment, ginger can be added in a range of from 0.25 wt % to 5 wt % to provide or assist the user with digestive support.

In an embodiment, Cocoa can be added in a range of from 0.25 wt % to 10 wt % provide a flavor, i.e. chocolate flavor.

In an embodiment, ginseng can be added in a range of from 0.5 wt % to 35 wt % to provide or assist the user with Focus and immune system support.

In an embodiment, gotu kola root and/or gotu kola extract can be added in a range of from 0.5 wt % to 35 wt % to provide or assist the user with Focus.

In an embodiment, cannabidiol can be added in a range of from 0.1 wt % to 10 wt % to provide or assist the user with immune system support.

In an embodiment, tetrahydrocannabinol (also as "THC") can be added in a range of from 0.1 wt % to 10 wt % to provide or assist the user with relaxation, appetite stimulation and/or anti-nausea.

In another embodiment, a green tea based formulation can have one or more of the following constituents: green tea leaves, flowers, stems, seeds and/or roots; caffeine in a range of between 10 mg and 1000 mg, e.g. 40 mg to 415 mg; or 25 mg to 500 mg; or 400 mg to 450 mg; or 200 mg to 400 mg; for 300 mg to 415 mg; or 150 mg to 300 mg; humectants comprising Zemea® USP propanediol, glycerol, sorbitol, or polydextrose; NaCl; water in an amount up to 75 wt %, e.g. 50 wt % of content and a water activity in a range of from 0.99 to 0.001, e.g. 0.9 or less; and optionally up to 25 wt % cellulose and/or additional plant material, e.g. up to 5 wt % additional plant material harvested from *Stevia*. In an embodiment, additional plant material harvested from *Stevia* can be in part, substantially, in significant part or primarily leaves.

Water activity or $a_w$ as used herein, in additional to its ordinary and customary meaning, also means the partial vapor pressure of water in a substance divided by the standard state partial vapor pressure of water. The standard state herein means the partial vapor pressure of pure water at the same temperature. Using this particular definition, pure distilled water has a water activity of exactly one. Embodiments herein can have $a_w$ values to support more microorganisms, e.g. bacteria usually require at least 0.91, and fungi at least 0.7. Alternatively, the formulations herein can have an $a_w$ to inhibit or prevent the growth of such organisms.

In an embodiment, the green tea based formulation can be dry leaves and water can be added. The ingredients disclosed herein can be mixed together in any composition without limitation to ingredient type (whether present or not used), compositional range, weight range, volume range, percentage, or other metric. The constituents and/or components can be mixed, blended, or otherwise brought together in many ways. All ingredients and/or constituents can have a value in a formulation as optionally and as desired from 0 wt % to 90 wt %, or greater, or as the upper limit is determined by health considerations of a user.

In the second aspect of the invention, a green tea based formulation can have some, if not all, of the following constituents: green tea leaves, flowers, stems, seeds and/or roots; caffeine in a quantity between 40 mg and 415 mg; humectants comprising Zemea® USP propanediol, glycerol, sorbitol, or polydextrose; NaCl; water in an amount up to 50 wt % of content and a water activity of 0.9 or less; and optionally up to 25 wt % cellulose and/or additional plant material, e.g. up to 5 wt % additional plant material harvested from *Glycyrrhiza* root (licorice root).

In yet another embodiment, a green tea based formulation can have some, if not all, of the following constituents: green tea leaves, flowers, stems, seeds and/or roots; caffeine in a quantity between 40 mg and 415 mg; humectants comprising Zemea® USP propanediol, glycerol, sorbitol, or polydextrose; NaCl; water in an amount up to 50 wt % of content and a water activity of 0.9 or less; up to 5 wt % additional plant material harvested from *Stevia* (in part, substantially, in significant part or primarily leaves); additional natural flavorings and colorings.

In an embodiment, a green tea based formulation having some, if not all, of the following constituents: green tea leaves, flowers, stems, seeds and/or roots; caffeine in a quantity between 40 mg and 415 mg; humectants comprising Zemea® USP propanediol, glycerol, sorbitol, or polydextrose; NaCl; water in an amount up to 50 wt % of content and a water activity of 0.9 or less; up to 5 wt % additional plant material harvested from *Glycyrrhiza* root (licorice root); additional natural flavorings and colorings.

In another embodiment the fifth aspect of the invention, a green tea based formulation having some, if not all, of the following constituents: green tea leaves, flowers, stems, seeds and/or roots; caffeine in a quantity between 40 mg and 415 mg; humectants comprising Zemea® USP propanediol, glycerol, sorbitol, or polydextrose; NaCl; water in an amount up to 50 wt % of content and a water activity of 0.9 or less; up to 5 wt % additional plant material harvested from *Glycyrrhiza* root (licorice root); plant material harvested from *Cannabis sativa* (in part, substantially, in significant part or primarily flowers, leaves and stems), dried and ground.

Plant material harvested from *Cannabis sativa* (in part, substantially, in significant part or primarily flowers, leaves and stems), dried and ground can be used in any of the formulations disclosed herein. Formulations can also be free of *Cannabis sativa* (in part, substantially, in significant part or primarily flowers, leaves and stems).

In an embodiment of the invention, a green tea based formulation having some, if not all, of the following constituents: green tea leaves, flowers, stems, seeds and/or roots; b) caffeine in a quantity between 40 mg and 415 mg; humectants comprising Zemea® USP propanediol, glycerol, sorbitol, or polydextrose; NaCl; water in an amount up to 50 wt % of content and a water activity of 0.9 or less; up to 5 wt % additional plant material harvested from *Stevia* (in part, substantially, in significant part or primarily leaves); and plant material harvested from *Cannabis sativa* (in part, substantially, in significant part or primarily flowers, leaves and stems). In an embodiment, the plant material harvested from *Cannabis sativa* (in part, substantially, in significant part or primarily flowers, leaves and stems) can be dried and/or ground, or otherwise processed. A tetrahydrocannabinol (THC) constituent can be added to any composition herein. The tetrahydrocannabinol (THC) constituent can be in a natural state, an extract, process and/or modified from its natural form.

In yet another embodiment, a green tea based formulation having some, if not all, of the following constituents: green tea leaves, flowers, stems, seeds and/or roots; caffeine in a quantity between 40 mg and 415 mg; humectants comprising Zemea® USP propanediol, glycerol, sorbitol, or polydextrose; NaCl; water in an amount up to 50 wt % of content and a water activity of 0.9 or less; up to 5 wt % additional plant material harvested from *Glycyrrhiza* root (licorice root); additional natural flavorings and colorings; plant material harvested from *Cannabis sativa* (in part, substantially, in significant part or primarily flowers, leaves and stems), dried and ground.

In another embodiment of the invention, a green tea based formulation having some, if not all, of the following constituents: green tea leaves, flowers, stems, seeds and/or roots; caffeine in a quantity between 40 mg and 415 mg; humectants comprising Zemea® USP propanediol, glycerol, sorbitol, or polydextrose; NaCl; water in an amount up to 50 wt % of content and a water activity of 0.9 or less; up to 5 wt % additional plant material harvested from *Glycyrrhiza* root (licorice root); additional natural flavorings and colorings; plant material harvested from *Cannabis sativa* (in part, substantially, in significant part or primarily flowers, leaves and stems), dried and ground. In another embodiment of the invention, a green tea based formulation having some, if not all, of the following constituents: green tea leaves, flowers, stems, seeds and/or roots; caffeine in a quantity between 40 mg and 415 mg; humectants comprising Zemea® USP propanediol, glycerol, sorbitol, or polydextrose; NaCl; water in an amount up to 50 wt % of content and a water activity of 0.9 or less; up to 5 wt % additional plant material harvested from *Stevia* (in part, substantially, in significant part or primarily leaves); additional natural flavorings and colorings; plant material harvested from *Cannabis sativa* (in part, substantially, in significant part or primarily flowers, leaves and stems), dried and ground.

In an embodiment, the tea composition can have 95 wt % to 99 wt % plant material harvested from *Cannabis sativa* (in part, substantially, in significant part or primarily flowers, leaves and stems), dried and ground; up to 5 wt % plant material harvested from *Stevia* (in part, substantially, in significant part or primarily leaves); NaCl; Polydextrose; Natural flavorings; water in an amount up to 50 wt % of content; caffeine in a quantity between 40 mg and 500 mg; and specifically excluding nicotine. (formally provisional claim 4)

In an embodiment, the tea composition can have 95 wt % to 99 wt % plant material harvested from *Cannabis sativa* (in part, substantially, in significant part or primarily flowers, leaves and stems), dried and ground; up to 5 wt % plant material harvested from *Glycyrrhiza* root (licorice root); NaCl; Polydextrose; Natural flavorings; water in an amount up to 50 wt % of content; caffeine in a quantity between 40 mg and 500 mg; and specifically excluding nicotine. (formally provisional claim 5)

In an embodiment, the tea composition can have 65 wt % to 69 wt % plant material harvested from *Camellia sinensis* (in part, substantially, in significant part or primarily leaves and stems), dried and ground; a range of from 5 wt % to 30 wt % plant material harvested from *Cannabis sativa* (in part, substantially, in significant part or primarily flowers, leaves and stems), dried and ground; up to 5 wt % plant material harvested from *Stevia* (in part, substantially, in significant part or primarily leaves); NaCl; Zemea® USP propanediol; water in an amount up to 50 wt % of content; caffeine in a quantity between 40 mg and 500 mg; and specifically excluding nicotine. (formally provisional claim 9)

In an embodiment, the tea composition can have material from any one or more of *Camellia sinensis* (e.g. including tea, green tea, white tea, yellow tea, oolong, black tea), material from *Camellia sinensis* var. *sinensis* and material from *Camellia sinensis* var. *assamica*.

In an embodiment, the tea composition can have *Stevia* leaf (*Stevia rebaudiana*) and/or *Stevia* root (*Stevia rebaudiana*) and/or any derivatives of the *Stevia* plant. In an embodiment, the tea composition can have one or more humectants, such as Zemea USP propanediol, sorbital, propylene glycol or polydextrose. Humectants can be used individually or in combination. In an embodiment Zemea USP propanediol and polydextrose can be used. In another embodiment, any one or more of the following can be used as a humectant: sorbital, polydextrose, and propylene glycol.

In an embodiment, the tea composition can have licorice root.

In an embodiment, the tea composition can have caffeine. In an embodiment, the tea composition can be free of caffeine.

In an embodiment, the tea composition can be free of nicotine. In an embodiment, the tea composition can have nicotine.

In an embodiment the tea composition can have: 5 wt % to 95 wt % of a plant material harvested from one or more of *Camellia sinensis*, yerba mate, and peppermint; 0.25 wt % to 25 wt % of a green tea extract; up to 70 wt % a monk fruit extract, sodium gluconate, a lemon juice powder, a natural flavor and a honey powder; 0.15 wt % to 15% of a caffeine powder; the tea composition can be free of tobacco; the tea composition can be free of nicotine; and the tea composition can have water in a range of from 0 wt % to 10 wt %. In an embodiment, the tea composition can optionally have any one or more of the following: a PUREFRUIT™ Select™ or other monk fruit extract in a range of 0.025 wt % to 25 wt %; a *Stevia;* 0.25 wt % to 25 wt %, or 0.15 wt % to 25 wt % of an L-theanine; 0.05 wt %-1 wt % of an huperzine serrate; 0.1 wt % to 10 wt % of a maca extract; 0.5 wt %-35 wt. % of a gotu kola root; and 0.5 wt %-35 wt % of a ginseng.

In an embodiment the tea composition can have: 5 wt %-95 wt % plant material harvested from one or more of *Camellia sinensis*, chamomile, and peppermint; 0.25 wt %-25 wt % of green tea extract; up 70 wt % of one or more of a monk fruit extract, sodium gluconate, a lemon juice powder, a natural flavor, peppermint leaf powder and a honey powder; 0.15 wt %-25 wt % of a L-theanine; the tea composition can be free of tobacco; the tea composition can be free of nicotine; and the tea composition can have water in a range of from 0 wt %-10 wt %. In an embodiment, the tea composition can optionally have any one or more of the following: 0.025 wt %-25 wt % of a PUREFRUIT™ Select or a monk fruit extract; a *Stevia;* 0.5 wt %-35 wt % of a kava; 0.05 wt %-0.5 wt % of a melatonin; 0.25 wt %-5 wt % of a ginger; 0.5 wt %-35 wt % of a valerian root; 0.5 wt %-35 wt % of a lemon balm (*Melissa officinalis*); and 0.5 wt %-35 wt % of a skullcap (genus *Scutellaria*);

In an embodiment the tea composition can have: 5 wt % to 95 wt % of a plant material harvested from one or more of *Camellia sinensis, Cannabis sativa*, yerba mate, and peppermint; 0.25 wt % to 25 wt % of a green tea extract; up to 70 wt % of one or more of a sodium gluconate, monk fruit extract, peppermint leaf powder, a lemon juice powder, a natural flavor; and a honey powder; the tea composition can be free of tobacco; the tea composition can be free of nicotine; and the tea composition can have water in a range of from 0 wt % to 10 wt %. In an embodiment, the tea composition can optionally have any one or more of the following: 0.015 wt % to 15% of a caffeine powder; 0.25 wt % to 25 wt % of a green tea extract; 0.025 wt % to 25 wt % of a PUREFRUIT™ Select or a monk fruit extract; a *Stevia;* 0.1 wt % to 10 wt % of a cannabidiol (CBD); and 0.1 wt % to 10 wt % of a tetrahydrocannabinol (THC).

Any of the tea compositions disclosed herein can be a product, a consumer product, or can be part of a consumer product. Any of the tea compositions disclosed herein can be an herbal product. Any of the tea compositions disclosed herein can be a nutritional supplement. Any of the tea compositions disclosed herein can be a pharmaceutical. Any of the tea compositions disclosed herein can be can be ingested in part or wholly. Any of the tea compositions disclosed herein can be impart a flavor to a user when administered orally.

Any of the tea compositions disclosed herein can impart an active ingredient, supplement, additive and/or compound and/or molecule for ingestion and/or absorption and/or adsorption by a user. Any of the tea compositions disclosed herein can impart an active ingredient to a user by mass transfer into the user's saliva.

In an embodiment, the tea composition can impart a flavor and/or effect to a user. In an embodiment, the effect upon a user occurs when the tea composition is administered orally.

In an embodiment the tea composition can impart an active ingredient, supplement, additive and/or compound and/or molecule for ingestion and/or absorption and/or absorption by a user. In an embodiment, the tea composition can impart an active ingredient to a user by mass transfer into the user's saliva. In embodiments, the tea compositions disclosed herein can be ingested in part or wholly.

A product can have any of the tea compositions disclosed herein. An herbal product can have any of the tea compositions disclosed herein. A nutritional supplement can have any of the tea compositions disclosed herein. A pharmaceutical can have any of the tea compositions disclosed herein.

In an embodiment, the tea composition can be packaged in a small pouch that is designed to lie inside the mouth, between the cheek and gum. In another embodiment, the tea composition can be packaged loosely inside a container, to be administered as a chewable product.

BRIEF DESCRIPTION OF THE DRAWINGS

The present invention in its several aspects and embodiments solves the problems discussed herein and significantly advances the technology of tea, packaging and administration of formulations having tea. The present invention can become more fully understood from the detailed description and the accompanying drawings, wherein:

FIG. 1A is a three-dimensional view of a filled pouch.

FIG. 1B is a three-dimensional view of cross-section of curved pouch.

FIG. 9 is a two-dimensional side view of rectangle-shaped pouch.

Herein, like reference numbers in one figure refer to like reference numbers in another figure.

Figure 2A:
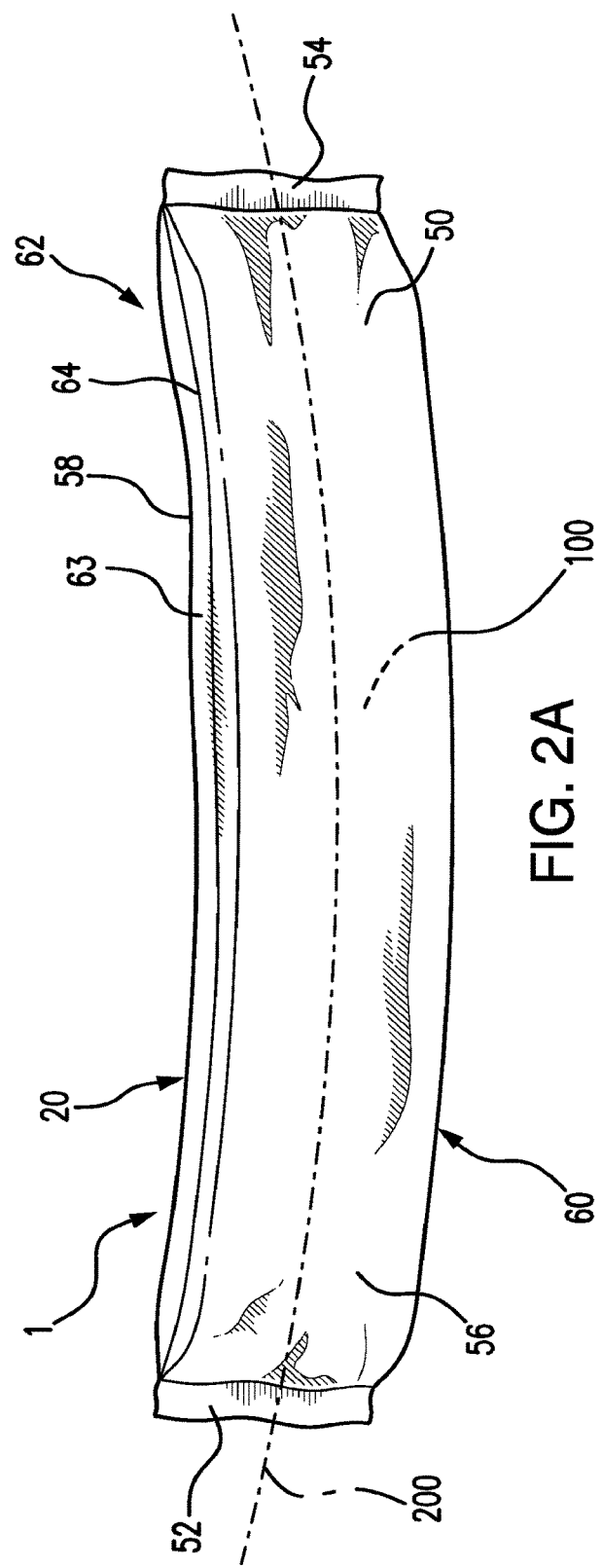
FIG. 2A is a side view of curved pouch.

The disclosed formulations, products and containers herein are not limited regarding any particular shape and/or form of manufacture.

DETAILED DESCRIPTION OF THE INVENTION

The formulations herein comprising green tea can be enjoyed for taste and/or as gastronomic and/or food experience and can also provide health benefits. Green tea compositions, mixtures and formulations (used synonymously herein), like many other tea products, can be steeped in hot water creating a drink which we shall refer to as "green tea drink" to differentiate from green tea, the flora. In an embodiment loose whole, dried green tea leaves can be placed directly in a receptacle and hot water is poured on top of the leaves.

The formulations disclosed herein can in the many and varied embodiments set forth provide enjoyment, health benefits, caffeine and other benefits of placing the moist tea leaves between lip and gum, cheek and gum, chewing, and swallowing the loose greet tea leaves and by ingestion and absorption deriving the flavor, health benefits, caffeine and other benefits and appreciation from the green tea leaves and any other constituents of a formulation. In an embodiment, the tea leaves can be moistened by water, oil or other means external to the leaf and/or have an internal water content in a range of from 1 wt % up to 75 wt % prior to placement in the mouth.

The formulations disclosed herein provide people access to the health benefits of green tea without the necessity of having to carry and hold a scalding cup of water in which to steep the green tea, and saves the user the time necessary to make steeped tea. It also provides a pleasurable way to enjoy the formulations not previously available.

The present invention makes available to a user the constituents and attributes of green tea, including caffeine, which is naturally existing in green tea and can be enhanced in the formulation to create a healthy alternative to people who use caffeine as a stimulant. The caffeine can be enhanced by adding additional caffeine to the formulation and/or adding other constituents to magnify the effect of the caffeine at whatever level is used whether a natural level or one achieved by adding more caffeine to the formulation. The present invention can offer a caffeine level to be ingested by the user similar or equal to a cup of coffee, caffeinated carbonated beverages and/or a so-called energy drink and provide the health benefits of green tea.

The present invention also offers an alternative to people, including professional athletes, who serve as poor role models to children by virtue of the fact that they dip tobacco snuff and chew loose leaf tobacco which offer nicotine as a stimulant. The formulations herein can be tobacco free and/or contain no tobacco. However, tobacco can be included optionally in any formulation herein.

The formulations herein can be nicotine free and/or contain no nicotine. However, nicotine can be included optionally in any formulation herein.

The formulations herein can solve over-indulgence by younger adults in particular in energy drinks that are high in calories and can be imbibed quickly. The present invention, in embodiments, can have no calories, or few calories as compared to energy drinks and typical carbonated beverages having a sweetener.

The present invention offers an alternative to people, who would like the taste and feel of a product they can chew, suck on, place between lip and gum and cheek and gum, and which unlike tobacco does not require spitting. Unlike tobacco which has proven to have harmful health effects, there are no commonly demonstrated harmful effects of green tea either swallowing the juice (ingestion) or absorbing the properties of green tea through cheek, lip and gum membranes.

The present invention is a moist green tea which offers people a healthy, clean, pleasurable way to enjoy the benefits of green tea which can includes, but is not limited to, caffeine. The formulations disclosed herein can also be decaffeinated. The formulations disclosed herein can comprise green tea (which can include flowers, leaves, stems, seeds, and roots), a humectant which can be defined as Zemea® USP propanediol, glycerol, sorbitol, or polydextrose and which can be used to maintain moisture, stabilize the product, provide a preservative action, and modify flavor, water, NaCl, and additives.

The present invention can comprise a moist green tea which offers people a healthy, clean, pleasurable way to enjoy the benefits of green tea which includes, but is not limited to, caffeine. The formulation for the present invention can be comprised of green tea (which can include flowers, leaves, stems, seeds, and roots), a humectant which can be defined as Zemea® USP propanediol, glycerol, sorbitol, or polydextrose and which can be used to maintain moisture, stabilize the product, provide a preservative action, and modify flavor, water, NaCl, and additives. In addition, one iteration of the present invention can include *Cannabis sativa* (in part, substantially, in significant part or primarily flowers, leaves and stems). There are two states which have legalized the use of *Cannabis sativa* under certain restrictions any iteration of the present invention which contains *Cannabis sativa* will only be manufactured and distributed under lawful conditions. The health benefits for certain categories of illness to access to *Cannabis sativa* have been well-documented medically, scientifically and anecdotally. Any iteration of the present invention which includes *Cannabis sativa* would be for lawful purposes only.

In an embodiment, the formulations disclosed herein can comprise green tea, water, NaCl, Zemea® or another humectant, and other additives including, but not limited to, mint as a natural flavoring.

In an embodiment, the formulations disclosed herein can comprise green tea, water, NaCl, Zemea® or another humectant, *Stevia* or licorice root, *Cannabis sativa*, and other additives including, but not limited to, mint as a natural flavoring.

In an embodiment, the formulations disclosed herein can comprise green tea, water, NaCl, Zemea® or another humectant, and other additives including, but not limited to, rebaudioside.

In an embodiment, the formulations disclosed herein can comprise green tea, water, NaCl, Zemea® or another humectant, *Stevia* or licorice root, *Cannabis sativa*, and other additives including, but not limited to, rebaudioside.

In an embodiment, the formulations disclosed herein can comprise green tea, water, NaCl, Zemea® or another humectant, and other additives including, but not limited to, cinnamon as a natural flavoring and for related health benefits.

In an embodiment, the formulations disclosed herein can comprise green tea, water, NaCl, Zemea® or another humectant, *Stevia* or licorice root, *Cannabis sativa*, and other additives including, but not limited to, cinnamon as a natural flavoring and for related health benefits.

In an embodiment, the formulations disclosed herein can comprise green tea, water, NaCl, Zemea® or another humectant, and other additives including, but not limited to, green tea extract as a natural flavoring and for health benefits and for the addition of caffeine.

In an embodiment, the formulations disclosed herein can comprise green tea, water, NaCl, Zemea® or another humectant, *Stevia* or licorice root, *Cannabis sativa*, and other additives including, but not limited to, green tea extract as a natural flavoring and for health benefits and for the addition of caffeine.

In an embodiment, the formulations disclosed herein can comprise green tea, water, NaCl, Zemea® or another humectant, and other additives including, but not limited to, coffee bean extract as a natural flavoring and for the addition of caffeine.

In an embodiment, the formulations disclosed herein can comprise green tea, water, NaCl, Zemea® or another humectant, *Stevia* or licorice root, *Cannabis sativa*, and other additives including, but not limited to, coffee bean extract as a natural flavoring and for the addition of caffeine.

In an embodiment, the formulations disclosed herein can comprise green tea, water, NaCl, Zemea® or another humectant, and other additives including, but not limited to, propolis.

In an embodiment, the formulations disclosed herein can comprise green tea, water, NaCl, Zemea® or another humectant, *Stevia* or licorice root, *Cannabis sativa*, and other additives including, but not limited to, propolis.

In an embodiment, the formulations disclosed herein can comprise green tea, water, NaCl, Zemea® or another humectant, and other additives including, but not limited to, bee pollen as a natural flavoring and for related health benefits.

In an embodiment, the formulations disclosed herein can comprise green tea, water, NaCl, Zemea® or another humectant, *Stevia* or licorice root, *Cannabis sativa*, and other additives including, but not limited to, bee pollen as a natural flavoring and for related health benefits.

In an embodiment, the formulations disclosed herein can comprise green tea, water, NaCl, Zemea® or another humectant, and other additives including, but not limited to, milk thistle extract.

In an embodiment, the formulations disclosed herein can comprise green tea, water, NaCl, Zemea® or another humectant, *Stevia* or licorice root, *Cannabis sativa*, and other additives including, but not limited to, milk thistle extract.

In an embodiment, the formulations disclosed herein can comprise green tea, water, NaCl, Zemea® or another humectant, and other additives including, but not limited to, guarana.

In an embodiment, the formulations disclosed herein can comprise green tea, water, NaCl, Zemea® or another humectant, *Stevia* or licorice root, *Cannabis sativa*, and other additives including, but not limited to, guarana.

In an embodiment, the formulations disclosed herein can comprise green tea, water, NaCl, Zemea® or another humectant, and other additives including, but not limited to, ginseng as a natural flavoring and for related health benefits.

In an embodiment, the formulations disclosed herein can comprise green tea, water, NaCl, Zemea® or another humectant, *Stevia* or licorice root, *Cannabis sativa*, and other additives including, but not limited to, ginseng as a natural flavoring and for related health benefits.

In an embodiment, the formulations disclosed herein can comprise green tea, water, NaCl, Zemea® or another humectant, and other additives including, but not limited to, rose hips as a natural flavoring.

In an embodiment, the formulations disclosed herein can comprise green tea, water, NaCl, Zemea® or another humectant, *Stevia* or licorice root, *Cannabis sativa*, and other additives including, but not limited to, rose hips as a natural flavoring.

In an embodiment, the formulations disclosed herein can comprise green tea, water, NaCl, Zemea® or another humectant, and other additives including, but not limited to, pomegranate extract as a natural flavoring and for related health benefits.

In an embodiment, the formulations disclosed herein can comprise green tea, water, NaCl, Zemea® or another humectant, *Stevia* or licorice root, *Cannabis sativa*, and other additives including, but not limited to, pomegranate extract as a natural flavoring and for related health benefits.

In an embodiment, the formulations disclosed herein can comprise green tea, water, NaCl, Zemea® or another humectant, and other additives including, but not limited to, acai berry extract as a natural flavoring and for related health benefits.

In an embodiment, the formulations disclosed herein can comprise green tea, water, NaCl, Zemea® or another humectant, *Stevia* or licorice root, *Cannabis sativa*, and other additives including, but not limited to, acai berry extract as a natural flavoring and for related health benefits.

In an embodiment, the formulations disclosed herein can comprise green tea, water, NaCl, Zemea® or another humectant, and other additives including, but not limited to, grape seed extract as a natural flavoring.

In an embodiment, the formulations disclosed herein can comprise green tea, water, NaCl, Zemea® or another humectant, *Stevia* or licorice root, *Cannabis sativa*, and other additives including, but not limited to, grape seed extract as a natural flavoring.

In an embodiment, the formulations disclosed herein can comprise green tea, water, NaCl, Zemea® or another humectant, and other additives including, but not limited to, Yerba mate or mate extract.

In an embodiment, the formulations disclosed herein can comprise green tea, water, NaCl, Zemea® or another humectant, *Stevia* or licorice root, *Cannabis sativa*, and other additives including, but not limited to, Yerba mate or mate extract.

In an embodiment, the formulations disclosed herein can comprise green tea, water, NaCl, Zemea® or another humectant, and other additives including, but not limited to, kava (*Piper methysticum*).

In an embodiment, the formulations disclosed herein can comprise green tea, water, NaCl, Zemea® or another humectant, *Stevia* or licorice root, *Cannabis sativa*, and other additives including, but not limited to, kava (*Piper methysticum*).

In an embodiment, the formulations disclosed herein can comprise green tea, water, NaCl, Zemea® or another humectant, and other additives including, but not limited to, passion flower.

In an embodiment, the formulations disclosed herein can comprise green tea, water, NaCl, Zemea® or another humectant, *Stevia* or licorice root, *Cannabis sativa*, and other additives including, but not limited to, passion flower.

In an embodiment, the formulations disclosed herein can comprise green tea, water, NaCl, Zemea® or another humectant, and other additives including, but not limited to, lemon balm (*Melissa officinalis*) or lemon extract as a natural flavoring.

In an embodiment, the formulations disclosed herein can comprise green tea, water, NaCl, Zemea® or another humectant, *Stevia* or licorice root, *Cannabis sativa*, and other additives including, but not limited to, lemon balm (*Melissa officinalis*) or lemon extract as a natural flavoring.

In an embodiment, the formulations disclosed herein can comprise green tea, water, NaCl, Zemea® or another humectant, and other additives including, but not limited to, valerian (*Valeriana officinalis*).

In an embodiment, the formulations disclosed herein can comprise green tea, water, NaCl, Zemea® or another humectant, *Stevia* or licorice root, *Cannabis sativa*, and other additives including, but not limited to, valerian (*Valeriana officinalis*).

In an embodiment, the formulations disclosed herein can comprise green tea, water, NaCl, Zemea® or another humectant, and other additives including, but not limited to, skullcap (genus *Scutellaria*).

In an embodiment, the formulations disclosed herein can comprise green tea, water, NaCl, Zemea® or another humectant, *Stevia* or licorice root, *Cannabis sativa*, and other additives including, but not limited to, skullcap (genus *Scutellaria*).

In an embodiment, the formulations disclosed herein can comprise green tea, water, NaCl, Zemea® or another humectant, and other additives including, but not limited to, cranberry as a natural flavoring and for related health benefits.

In an embodiment, the formulations disclosed herein can comprise green tea, water, NaCl, Zemea® or another humectant, *Stevia* or licorice root, *Cannabis sativa*, and other additives including, but not limited to, cranberry as a natural flavoring and for related health benefits.

In an embodiment, the formulations disclosed herein can comprise green tea, water, NaCl, Zemea® or another humectant, and other additives including, but not limited to, guar gum.

In an embodiment, the formulations disclosed herein can comprise green tea, water, NaCl, Zemea® or another humectant, *Stevia* or licorice root, *Cannabis sativa*, and other additives including, but not limited to, guar gum.

In an embodiment, the formulations disclosed herein can comprise green tea, water, NaCl, Zemea® or another humectant, and other additives including, but not limited to, rosemary.

In an embodiment, the formulations disclosed herein can comprise green tea, water, NaCl, Zemea® or another humectant, *Stevia* or licorice root, *Cannabis sativa*, and other additives including, but not limited to, rosemary.

In an embodiment, the formulations disclosed herein can comprise green tea, water, NaCl, Zemea® or another humectant, and other additives including, but not limited to, wintergreen.

In an embodiment, the formulations disclosed herein can comprise green tea, water, NaCl, Zemea® or another humectant, *Stevia* or licorice root, *Cannabis sativa*, and other additives including, but not limited to, wintergreen.

In an embodiment, the formulations disclosed herein can comprise green tea, water, NaCl, Zemea® or another humectant, and other additives including, but not limited to, mint as a natural flavoring.

In an embodiment, the formulations disclosed herein can comprise green tea, water, NaCl, Zemea® or another humectant, *Stevia* or licorice root, *Cannabis sativa*, and other additives including, but not limited to, mint as a natural flavoring.

In an embodiment, the formulations disclosed herein can comprise green tea, water, NaCl, Zemea® or another humectant, and other additives including, but not limited to, spearmint (*Mentha spicata*) as a natural flavoring.

In an embodiment, the formulations disclosed herein can comprise green tea, water, NaCl, Zemea® or another humectant, *Stevia* or licorice root, *Cannabis sativa*, and other additives including, but not limited to, spearmint (*Mentha spicata*) as a natural flavoring.

In an embodiment, the formulations disclosed herein can comprise green tea, water, NaCl, Zemea® or another humectant, and other additives including, but not limited to, wintergreen (*Gaultheria procumbens*) as a natural flavoring.

In an embodiment, the formulations disclosed herein can comprise green tea, water, NaCl, Zemea® or another humectant, *Stevia* or licorice root, *Cannabis sativa*, and other additives including, but not limited to, wintergreen (*Gaultheria procumbens*) as a natural flavoring.

The present invention, in all aspects, can be comprised of plant material (which can include flowers, leaves, stems, seeds, and roots), refers to tea, green tea, white tea, yellow tea, oolong, black tea, or any plant material harvested from *Camellia sinensis, Camellia sinensis* var. *sinensis* and/or *Camellia sinensis* var. *assamica* (tea), and/or *Cannabis sativa* (marijuana).

The present invention, in all aspects, can be intended to be produced as an intermediate moisture food, comprising a water content of 10-40 wt % and a water activity ranging from 0.6-0.9. This will maximize the comfort of keeping the product in the mouth, while minimizing bacterial growth which tends to occur at 0.91 water activity and higher.

The present invention, in all aspects, can be comprised of humectants which can be defined as of Zemea® USP propanediol, glycerol, sorbitol, or polydextrose which will be used to maintain moisture, stabilize the product, provide a preservative action and modify flavor.

The present invention, in all aspects, will contain Salt (NaCl) which can be added for both flavor and a preservative action.

In an example embodiment, the tea composition can have the following: yerba mate in a range of 1 wt %-60 wt %, or 23.80 wt % to 35.70 wt %, such as 10 wt %, 15 wt %, 20 wt %, 29.75 wt %; 30 wt %, or 40 wt %; PUREFRUIT™ Select and/or monk fruit extract and/or fruit extract in a range of 0.1 wt % to 5 wt %, or 0.2 wt % to 1 wt %, or 0.20 wt % to 0.30 wt %, or 0.1 wt % to 0.40 wt %, such as 0.1 wt %, 0.2 wt %, 0.25 wt %, 0.3 wt %, 0.35 wt %, 0.5 wt %; peppermint leaf in a range of 0.3 wt % to 35 wt %, or 1 wt % to 25 wt %, 2 wt % to 20 wt %, 3 wt % to 10 wt %, or 2.80 wt % to 4.20 wt %, such as 2.0 wt %, 2.5 wt %, 3.0 wt %, 3.50 wt %; 4.0 wt %, 4.5 wt %, 5 wt %, 10 wt %, 25 wt %; peppermint leaf powder in a range of 0.5 wt % to 50 wt %, or 0.75 wt % to 40 wt %, 1 wt % to 15 wt %, 10 wt % to 30 wt %, 5 wt % to 12 wt %, 6.00 wt % to 9.00 wt %, or 7.00 wt % to 8.00 wt %, such as 1 wt %, 3 wt %, 5 wt %, 5.5 wt %, 6.0 wt %, 7.0 wt %, 7.50 wt %, 8 wt %; 9 wt %, 10 wt %, or 14.5 wt %; green tea extract in a range of 0.5 wt % to 10 wt %, or 1.00 wt % to 5.00 wt %, or 2.00 wt % to 3.00 wt %, or 1.5 wt % to 6 wt %, such as 1 wt %, 1.5 wt %, 2 wt %, 2.50 wt %; 3.0 wt %, 3.5 wt %, 5 wt, 7.5 wt % or 9 wt %. green tea loose leaf in a range of 1 wt % to 75 wt %, or 1 wt % to 50 wt %, or 1 wt % to 25 wt %, or 5 wt % to 40 wt %, or 10 wt % to 25 wt %, or 10 wt % to 15 wt %, or 8.00 wt % to 12.00 wt %, such as 1 wt %, 5 wt %, 6.0 wt %, 10.00 wt %, 12.00 wt %, 15.00 wt %, 20 wt %, 25 wt %, or 30 wt %; Caffeine powder in a range of 0.1 wt % to 25 wt %, or 0.15 wt % to 25 wt %, or 0.2 wt % to 20 wt %, or 1 wt % to 10 wt %, or 1.2 wt % to 5 wt %, or 1.0 wt % to 2 wt %, or 1.2 wt % to 1.8 wt %, such as 1 wt %, 1.1 wt %, 1.2 wt %, 1.3 wt %, 1.5 wt %, 1.6 wt %, 1.8 wt %, 2 wt %, 2.2 wt %, 4 wt %, 6 wt %, or 10%; Sodium gluconate in a range of 0.01 wt % to 15 wt %, 0.05 wt % to 10 wt %, 0.25 wt % to 5 wt %, 0.3 wt % to 2 wt %, 0.40 wt % to 1 wt %, 0.40 wt % to 0.80 wt %, 0.40 wt % to 0.60 wt %, 0.50 wt % to 0.60 wt %, such as 0.01 wt %, 0.025 wt %, 0.05 wt %, 0.50 wt %, 0.75 wt %, 1 wt %, 1.25 wt %, 1.5 wt %, 3 wt %, 5 wt %, or 10 wt %; Lemon juice powder in a range of 1 wt % to 50 wt %, 1 wt % to 40 wt %, 2.0 wt % to 35 wt %, 2.5 wt % to 25 wt %, 5 wt % to 40 wt %, 2.5 wt % to 50 wt %, 3 wt % to 15 wt %, such as 2 wt %, 5 wt %, 7.5 wt %, 10 wt %, 12 wt %, 15 wt %, 20 wt %, 25 wt %, 30 wt %, 35 wt %, or 40 wt %; Natural flavor in a range of 0.01 wt % to 50 wt %, 0.05 wt % to 40 wt %, 0.075 wt % to 35 wt %, 1 wt % to 15 wt %, 4 wt % to 12.00 wt %, 5 wt % to 10 wt %, 6.00 wt % to 9.00 wt %, 7.00 wt % to 8.00 wt %, such as 0.5 wt %, 2.5 wt %, 4.0 wt %, 5.0 wt %, 6.0 wt %, 7.0 wt %, 7.5 wt %, 8.0 wt %, 8.5 wt %, 9 wt %, or 10 wt %; and Honey powder in a range of 0.5 wt % to 50 wt %, 1 wt % to 40 wt %, 1.2 wt % to 10 wt %, 5 wt % to 40 wt %, 8 wt % to 22 wt %, 9.60 wt % to 14.40 wt %, 10 wt % to 20 wt %, 10 wt % to 15 wt %, 11 wt % to 14 wt %, 12 wt % to 20 wt %, 8 wt % to 22 wt %, such as 5 wt %, 7.5 wt %, 8 wt %, 10 wt %, 11 wt %, 12 wt %, 13 wt %, 14 wt %, 15 wt %, 20 wt %, 25 wt %, 30 wt %, 35 wt %, or 40 wt %.

In an example embodiment, the tea composition can have any one or more of the following: yerba mate in a range of 1 wt %-60 wt %, or 23.80 wt % to 35.70 wt %, such as 10 wt %, 15 wt %, 20 wt %, 29.75 wt %; 30 wt %, or 40 wt %; PUREFRUIT™ Select and/or monk fruit extract and/or fruit extract in a range of 0.1 wt % to 5 wt %, or 0.2 wt % to 1 wt %, or 0.20 wt % to 0.30 wt %, or 0.1 wt % to 0.40 wt %, such as 0.1 wt %, 0.2 wt %, 0.25 wt %, 0.3 wt %, 0.35 wt %, 0.5 wt %; peppermint leaf in a range of 0.3 wt % to 35 wt %, or 1 wt % to 25 wt %, 2 wt % to 20 wt %, 3 wt % to 10 wt %, or 2.80 wt % to 4.20 wt %, such as 2.0 wt %, 2.5 wt %, 3.0 wt %, 3.50 wt %; 4.0 wt %, 4.5 wt %, 5 wt %, 10 wt %, 25 wt %; peppermint leaf powder in a range of 0.5 wt % to 50 wt %, or 0.75 wt % to 40 wt %, 1 wt % to 15 wt %, 10 wt % to 30 wt %, 5 wt % to 12 wt %, 6.00 wt % to 9.00 wt %, or 7.00 wt % to 8.00 wt %, such as 1 wt %, 3 wt %, 5 wt %, 5.5 wt %, 6.0 wt %, 7.0 wt %, 7.50 wt %, 8 wt %; 9 wt %, 10 wt %, or 14.5 wt %; green tea extract in a range of 0.5 wt % to 10 wt %, or 1.00 wt % to 5.00 wt %, or 2.00 wt % to 3.00 wt %, 1.5 wt % to 6 wt %, such as 1 wt %, 1.5 wt %, 2 wt %, 2.50 wt %; 3.0 wt %, 3.5 wt %, 5 wt, 7.5 wt % or 9 wt %. green tea loose leaf in a range of 1 wt % to 75 wt %, or 1 wt % to 50 wt %, or 1 wt % to 25 wt %, or 5 wt % to 40 wt %, or 10 wt % to 25 wt %, or 10 wt % to 15 wt %, or 8.00 wt % to 12.00 wt %, such as 1 wt %, 5 wt %, 6.0 wt %, 10.00 wt %, 12.00 wt %, 15.00 wt %, 20 wt %, 25 wt %, or 30 wt %; Caffeine powder in a range of 0.1 wt % to 25 wt %, or 0.15 wt % to 25 wt %, or 0.2 wt % to 20 wt %, or 1 wt % to 10 wt %, or 1.2 wt % to 5 wt %, or 1.0 wt % to 2 wt %, or 1.2 wt % to 1.8 wt %, such as 1 wt %, 1.1 wt %, 1.2 wt %, 1.3 wt %, 1.5 wt %, 1.6 wt %, 1.8 wt %, 2 wt %, 2.2 wt %, 4 wt %, 6 wt %, or 10%; Sodium gluconate in a range of 0.01 wt % to 15 wt %, 0.05 wt % to 10 wt %, 0.25 wt % to 5 wt %, 0.3 wt % to 2 wt %, 0.40 wt % to 1 wt %, 0.40 wt % to 0.80 wt %, 0.40 wt % to 0.60 wt %, 0.50 wt % to 0.60 wt %, such as 0.01 wt %, 0.025 wt %, 0.05 wt %, 0.50 wt %, 0.75 wt %, 1 wt %, 1.25 wt %, 1.5 wt %, 3 wt %, 5 wt %, or 10 wt %; Lemon juice powder in a range of 1 wt % to 50 wt %, 1 wt % to 40 wt %, 2.0 wt % to 35 wt %, 2.5 wt % to 25 wt %, 5 wt % to 40 wt %, 2.5 wt % to 50 wt %, 3 wt % to 15 wt %, such as 2 wt %, 5 wt %, 7.5 wt %, 10 wt %, 12 wt %, 15 wt %, 20 wt %, 25 wt %, 30 wt %, 35 wt %, or 40 wt %; Natural flavor in a range of 0.01 wt % to 50 wt %, 0.05 wt % to 40 wt %, 0.075 wt % to 35 wt %, 1 wt % to 15 wt %, 4 wt % to 12.00 wt %, 5 wt % to 10 wt %, 6.00 wt % to 9.00 wt %, 7.00 wt % to 8.00 wt %, such as 0.5 wt %, 2.5 wt %, 4.0 wt %, 5.0 wt %, 6.0 wt %, 7.0 wt %, 7.5 wt %, 8.0 wt %, 8.5 wt %, 9 wt %, or 10 wt %; and Honey powder in a range of 0.5 wt % to 50 wt %, 1 wt % to 40 wt %, 1.2 wt % to 10 wt %, 5 wt % to 40 wt %, 8 wt % to 22 wt %, 9.60 wt % to 14.40 wt %, 10 wt % to 20 wt %, 10 wt % to 15 wt %, 11 wt % to 14 wt %, 12 wt % to 20 wt %, 8 wt % to 22 wt %, such as 5 wt %, 7.5 wt %, 8 wt %, 10 wt %, 11 wt %, 12 wt %, 13 wt %, 14 wt %, 15 wt %, 20 wt %, 25 wt %, 30 wt %, 35 wt %, or 40 wt %.

In another embodiment, the tea composition can have any one or more of the following: yerba mate in a range of 1 wt %-60 wt %, or 23.80 wt % to 35.70 wt %, such as 10 wt %, 15 wt %, 20 wt %, 29.75 wt %; 30 wt %, or 40 wt %; monk fruit extract and/or fruit extract in a range of 0.1 wt % to 5 wt %, or 0.2 wt % to 1 wt %, or 0.20 wt % to 0.30 wt %, or 0.1 wt % to 0.40 wt %, such as 0.1 wt %, 0.2 wt %, 0.25 wt %, 0.3 wt %, 0.35 wt %, 0.5 wt %; a peppermint in a range of 0.5 wt % to 50 wt %, or 0.75 wt % to 40 wt %, 1 wt % to 15 wt %, 10 wt % to 30 wt %, 5 wt % to 12 wt %, 6.00 wt % to 9.00 wt %, or 7.00 wt % to 8.00 wt %, such as 1 wt %, 3 wt %, 5 wt %, 5.5 wt %, 6.0 wt %, 7.0 wt %, 7.50 wt %, 8 wt %; 9 wt %, 10 wt %, or 14.5 wt %; green tea in a range of 1 wt % to 75 wt %, or 1 wt % to 50 wt %, or 1 wt % to 25 wt %, or 5 wt % to 40 wt %, or 10 wt % to 25 wt %, or 10 wt % to 15 wt %, or 8.00 wt % to 12.00 wt %, such as 1 wt %, 5 wt %, 6.0 wt %, 10.00 wt %, 12.00 wt %, 15.00 wt %, 20 wt %, 25 wt %, or 30 wt %; caffeine 0.01 wt % to 25 wt %, or 0.15 wt % to 25 wt %, or 0.2 wt % to 20 wt %, or 1 wt % to 10 wt %, or 1.2 wt % to 5 wt %, or 1.0 wt % to 2 wt %, or 1.2 wt % to 1.8 wt %, such as 1 wt %, 1.1 wt %, 1.2 wt %, 1.3 wt %, 1.5 wt %, 1.6 wt %, 1.8 wt %, 2 wt %, 2.2 wt %, 4 wt %, 6 wt %, or 10%; Sodium gluconate in a range of 0.01 wt % to 15 wt %, 0.05 wt % to 10 wt %, 0.25 wt % to 5 wt %, 0.3 wt % to 2 wt %, 0.40 wt % to 1 wt %, 0.40 wt % to 0.80 wt %, 0.40 wt % to 0.60 wt %, 0.50 wt % to 0.60 wt %, such as 0.01 wt %, 0.025 wt %, 0.05 wt %, 0.50 wt %, 0.75 wt %, 1 wt %, 1.25 wt %, 1.5 wt %, 3 wt %, 5 wt %, or 10 wt %; lemon juice 1 wt % to 50 wt %, 1 wt % to 40 wt %, 2.0 wt % to 35 wt %, 2.5 wt % to 25 wt %, 5 wt % to 40 wt %, 2.5 wt % to 50 wt %, 3 wt % to 15 wt %, such as 2 wt %, 5 wt %, 7.5 wt %, 10 wt %, 12 wt %, 15 wt %, 20 wt %, 25 wt %, 30 wt %, 35 wt %, or 40 wt %; natural flavor or artificial flavor in a range of 0.01 wt % to 50 wt %, 0.05 wt % to 40 wt %, 0.075 wt % to 35 wt %, 1 wt % to 15 wt %, 4 wt % to 12.00 wt %, 5 wt % to 10 wt %, 6.00 wt % to 9.00 wt %, 7.00 wt % to 8.00 wt %, such as 0.5 wt %, 2.5 wt %, 4.0 wt %, 5.0 wt %, 6.0 wt %, 7.0 wt %, 7.5 wt %, 8.0 wt %, 8.5 wt %, 9 wt %, or 10 wt %; and sweetener and/or flavorant and/or honey in a range of 0.5 wt % to 50 wt %, 1 wt % to 40 wt %, 1.2 wt % to 10 wt %, 5 wt % to 40 wt %, 8 wt % to 22 wt %, 9.60 wt % to 14.40 wt %, 10 wt % to 20 wt %, 10 wt % to 15 wt %, 11 wt % to 14 wt %, 12 wt % to 20 wt %, 8 wt % to 22 wt %, such as 5 wt %, 7.5 wt %, 8 wt %, 10 wt %, 11 wt %, 12 wt %, 13 wt %, 14 wt %, 15 wt %, 20 wt %, 25 wt %, 30 wt %, 35 wt %, or 40 wt %.

In an embodiment, a yerba mate base tea composition can be used. The yerba mate base tea composition can be composed at least in part, or wholly, of plant materials such as yerba mate (3-60 wt %), green tea leaf (*Camellia sinensis*) and/or green tea material (1-50 wt %), peppermint leaf (0.3-35%), peppermint leaf powder (0.75%-40%).

Optionally, a tea composition can use the yerba mate base tea composition with the addition of any one or more of the following ingredients: L-theanine, e.g. in a range of 0.15 wt % to 25 wt %, or 15 wt % to 25 wt %; huperzine serrate, e.g. in a range of 0.05 wt % to 1 wt %; maca extract, e.g. in a range of 0.1 wt % to 10 wt % (for a user's vitality); gotu kola root, e.g. in a range of 0.5 wt % to 35 wt %; and ginseng, e.g. in a range of −0.5 wt % to 35%.

A tea composition can have lemon juice powder (2.5 wt %-50 wt %), sodium gluconate (0.05 wt %-5 wt %), caffeine powder (0.15 wt % 15 wt %), honey powder (1.2 wt %-40 wt %), natural flavors (0.75 wt %-35 wt %).

In an embodiment, a chamomile base tea composition can be used. The chamomile base tea composition can be composed at least in part, or wholly, of plant materials such as chamomile (3-60 wt %), green tea leaf (*Camellia sinensis*) (1-50 wt %), peppermint leaf (0.3-35%), peppermint leaf powder (0.75%-40%).

Optionally, a tea composition can use the chamomile base tea composition with the addition of any one or more of the following ingredients: kava (*Piper methysticum*), e.g. in a range from 0.5 wt % to 35 wt %; melatonin, e.g. in a range from 0.05 wt % to 0.5 wt %; ginger, e.g. in a range from 0.25 wt % to 5 wt %; valerian root, e.g. in a range from 0.5 wt % to 35 wt %; lemon balm (*Melissa officinalis*), e.g. in a range from 0.5 wt %-35 wt %; and skullcap (genus *Scutellaria*), e.g. in a range from 0.5 wt %-35 wt %.

In an embodiment, the tea composition can have lemon juice powder (2.5 wt %-50 wt %), sodium gluconate (0.05 wt %-5 wt %), caffeine powder (0.15 wt % 15 wt %), honey powder (1.2 wt %-40 wt %), natural flavors (0.75 wt %-35 wt %).

In an embodiment, a marijuana based tea composition can be used. The marijuana base tea composition can be composed at least in part, or wholly, of plant materials such as marijuana (*Cannabis sativa*) (3 wt % to 60 wt %), yerba mate (3 wt % to 60 wt %), green tea leaf (*Camellia sinensis*) (1 wt % to 50 wt %), peppermint leaf (0.3 wt % to 35%), peppermint leaf powder (0.75 wt % to 40 wt %).

Optionally, a tea composition can use the marijuana base tea composition with the addition of any one or more of the following ingredients: cannabidiol (CBD) in a range of wt % to 10 wt % and tetrahydrocannabinol (THC) in a range of 0.1 wt % to 10 wt %.

In other embodiments any one or more of the following ingredients can be used in any of the tea compositions disclosed herein at any desired wt % of the tea composition: L-theanine, e.g. in a range of 0.15% to 25%; huperzine serrate, e.g. in a range of 0.05%-1%; maca extract, e.g. in a range of 0.1% to 10%; gotu kola root, e.g. in a range of 0.5-35%; ginseng, e.g. in a range of 0.5-35%; kava, e.g. in a range of 0.5-35%; melatonin, e.g. in a range of 0.05-0.5%; ginger, e.g. in a range of 0.25-5%; valerian root, e.g. in a range of 0.5-35%; lemon balm (*Melissa officinalis*), e.g. in a range of 0.5-35%; skullcap (genus *Scutellaria*), e.g. in a range of 0.5-35%; cannabidiol (CBD), e.g. in a range of 0.1% to 10%; and tetrahydrocannabinol (THC), e.g. in a range of 0.1 to 10%.

In other embodiments any one or more of the following ingredients can be used in any of the tea compositions disclosed herein at any desired wt % of the tea composition: yerba mate (*Ilex paraguariensis*, a type of holly), e.g. in a concentration of less than 60 wt %; green tea extract, e.g. in a concentration of 0.25 wt % to 25 wt %; caffeine, e.g. in a concentration of 0.15 wt % to 15 wt %; PUREFRUIT™ Select, monk fruit extract (or other monk fruit extract), e.g. in a concentration of less than 70 wt %; sodium gluconate (to inhibit bitterness), e.g. in a concentration of 0.05 wt % to 5 wt %; lemon juice powder, e.g. in a concentration of 2.5 wt % to 50 wt %; natural flavors, e.g. in a concentration of 0.75 wt % to 35 wt %; additional flavor, e.g. in a concentration of less than 50 wt %; cocoa, e.g. in a concentration of 0.25 wt % to 10 wt %; acai berry (powder or extract), e.g. in a concentration of 0.25 wt % to 10 wt %; rose hips, e.g. in a concentration of 0.25 wt % to 10 wt %; and coffee bean, e.g. in a concentration 0.25 wt % to 10 wt %.

In an embodiment the composition and/or tea composition and/or product composition can have: 5 wt % to 95 wt % of a plant material harvested from one or more of *Camellia sinensis*, yerba mate, a peppermint, a peppermint leaf and a peppermint leaf powder; 0.25 wt % to 25 wt % of a green tea extract; up 70 wt % of content of one or more of a monk fruit extract, sodium gluconate, a lemon juice powder, a natural flavor and a honey powder; 0.15 wt % to 15% of a caffeine powder; and said composition having water in a range of from 0 wt % to 10 wt %. In an embodiment, any one or more types of a peppermint can be used. For example a peppermint can be used which is a pure plant material, or a part or portion of a peppermint plant, or a leave of a peppermint plant. A peppermint can also be powder derived from a source of peppermint, such as a peppermint leaf from which a peppermint leaf powder is derived. A peppermint can also be a grinding, cutting or shaving of a peppermint plant or other source. A peppermint can also be a peppermint extract, oil, plant derivative, processed flavor or compound. Any peppermint flavor or source of peppermint flavor can be used. This disclosure is to be broadly construed as to any type of flavor and the material and/or form by which a flavor is imparted to the composition and/or tea composition and/or product.

In an embodiment the composition and/or tea composition and/or product composition can have: 5 wt % to 95 wt % plant material harvested from one or more of *Camellia sinensis*, chamomile, a peppermint, a peppermint leaf and a peppermint leaf powder; 0.25 wt % to 25 wt % of green tea extract; up 70 wt % of one or more of a monk fruit extract, sodium gluconate, a lemon juice powder, a natural flavor, and a honey powder; 0.15 wt % to 25 wt % of a L-theanine; and said composition having water in a range of from 0 wt % to 10 wt %.

In an embodiment the composition and/or tea composition and/or product composition can have: 5 wt % to 95 wt % of a plant material harvested from one or more of *Camellia sinensis, Cannabis sativa*, yerba mate, a peppermint, a peppermint leaf and a peppermint leaf power; 0.25 wt % to 25 wt % of a green tea extract; up to 70 wt % of one or more of a monk fruit extract, sodium gluconate, a lemon juice powder, a natural flavor; and a honey powder; and said composition having water in a range of from 0 wt % to 10 wt %.

Any composition herein can have any one or more of the following additives, flavors and extracts: ginger, coffee, coffee bean, gotu kola root, gotu kola extract, kola nut, cocoa, guarana, yerba mate and yerba mate extract, macs extract, L-theanine, *Huperzia serrata*, huperzine serrate, milk thistle leaf, milk thistle powder milk thistle extract, blueberry extract, grape extract, green tea or green tea extract, propolis, turmeric, fennel, gingko biloba, ginseng, rose hips, pomegranate, acai berry, grape seed, lemon, lemon peel, lemon juice powder, cranberry, mint, cinnamon, cocoa, green tea, mint, spearmint (*Mentha spicata*), wintergreen (*Gaultheria procumbens*), rosemary, passion flower, *Glycyrrhiza* root (licorice root), cocoa, ginger, bee pollen, peppermint, peppermint leaf powder, lemon balm (*Melissa officials*), *Cannabis sativa*, tetrahydrocannabinol (THC), cannabidiol (CBD), propolis, honey, honey powder, monk fruit extract, PUREFRUIT™ Select, *Stevia*, agave, fruit juice concentrates, kava (*Piper methysticum*), chamomile, melatonin, valerian (*Valeriana officinalis*), valerian root, lemon balm (*Melissa officinalis*), skullcap (genus *Scutellaria*) flax seed oil, hemp seed oil, tartaric, malic acid, citric acid, and sodium gluconate.

FIG. 1A is a three-dimensional view of a filled pouch 1. The pouch 1 in the FIG. 1A example can be filled with any of the tea compositions disclosed herein. FIG. 1A shows a pouch 1 having a pouch cavity 100 into which a tea composition can be contained. The pouch 1 can have a first end 52 and a second end 54. The first end 52 can be a closed end and the second end 54 can be a closed end. In an embodiment, the first end 52 can be a sealed end. The second end 54 can also be a sealed end. Optionally, the ends can also be formed by the folding of material, sewing, application of adhesive, weaving, heating other means of closing or sealing a pouch end.

The pouch 1 can have an upper pouch 56 and a lower pouch 58. In an embodiment, the upper and lower pouch can be connected by one or more side walls.

The pouch 1 can have a first side 60 having a first side wall 59. The first side 60 can have a first side wall 59 optionally having a first side pleat 57. The pouch 1 can also have a second side 62 having a second side wall 63. The second side wall 63 can optionally have a second side pleat 64 (FIG. 2A). The example of FIG. 1 shows a rectangular pouch 10. The pouch 1 can be made of pouch material 50.

In an embodiment, the pouch cavity 100 can be bounded by the upper pouch 56 and the lower pouch 58, the first end 52 and the second end 54, as well as the first side wall 59 and second side wall 63.

FIG. 1B is a three-dimensional view of cross-section of a curved pouch. FIG. 1B shows a tea composition 99 (also herein as composition 99 and contents 99) filling pouch cavity 100. Herein, the material filling the pouch cavity 100 are referred to as a contents 99, which for example can be the tea composition 99 and/or the composition 99.

FIG. 1B is a three-dimensional view of cross-section of a curved pouch 20 (also herein as gingival curved pouch 20). FIG. 1B is a three-dimensional view of a cross-section of the curved pouch 20. As shown in FIG. 2A, Each end of the pouch 1 is sealed and the contents of the pouch 1 are contained within the hollow space between the two sealed ends and the two side walls of the pouch. The pouch is curved gently upwards at an angle so that the bottom side of the pouch is a gently curved shape designed to mirror the curve of the lower jaw.

FIG. 2A is a two-dimensional side view of a curved pouch 20 (also herein as "gingival curved pouch 20). FIG. 2A is a side view of curved pouch. FIG. 2A is a side view of a gingival curved pouch 20. In an embodiment, the pouch can be formed to have a gingival curve 200. The gingival curved pouch 20 having the gingival curve 200 can be comfortably place in a user's mouth fitting nicely proximate to the users gum and/or inner lip. In an embodiment, the gingival curved pouch 20 is configured for ready accommodation proximate to a user's gingiva and/or alveolar mucosa. In another embodiment, the gingival curved pouch 20 is shaped for ready accommodation in a user's cheek area between the cheek and gum, such as proximate to the user's buccal mucosa, or between the user's buccal mucosa and a gingiva and/or alveolar mucosa.

Figure 2B:
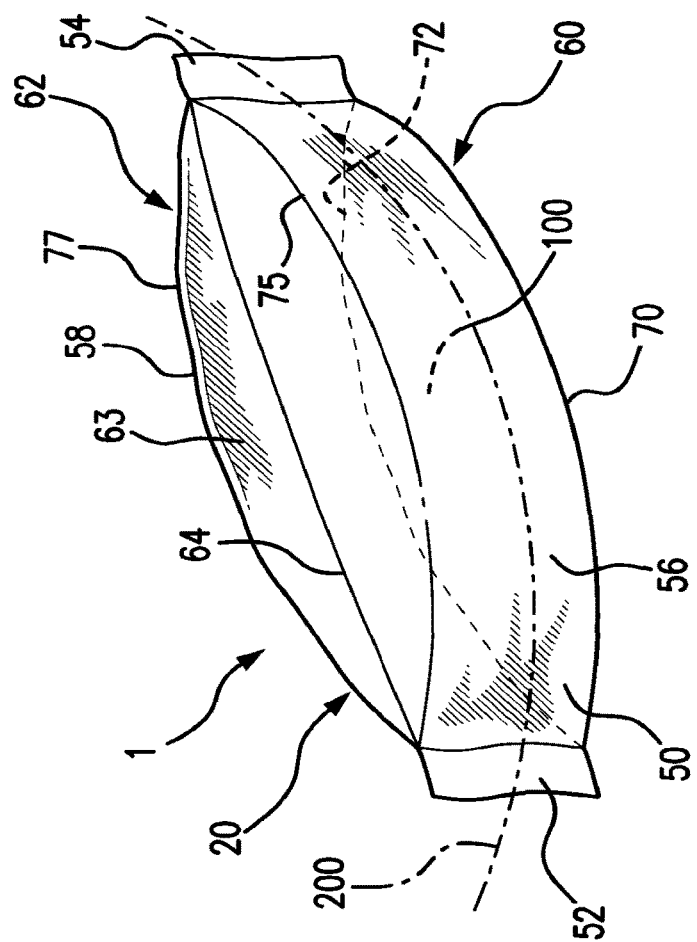
FIG. 2B is a two-dimensional side view of a gingival curved pouch.

FIG. 2B illustrates a first upper edge 70 and a first lower edge 72 of first side 60 curved parallel to the gingival curve 200. The second upper edge 75 and second lower edge 77 are also curved parallel to the gingival curve 200.

The gingival curve 200 can be any curve which accommodates a user's anatomy in a comfortable manner. In an embodiment, the gingival curve 200 can have an angle of arc between 0° and 180°, such as in non-limiting example, between 5° and 170°, 10° and 175, and 20° and 160°. In another embodiment, the angle of arc can be greater than 10°. In another, it can be less than 175°.

Figure 2C:
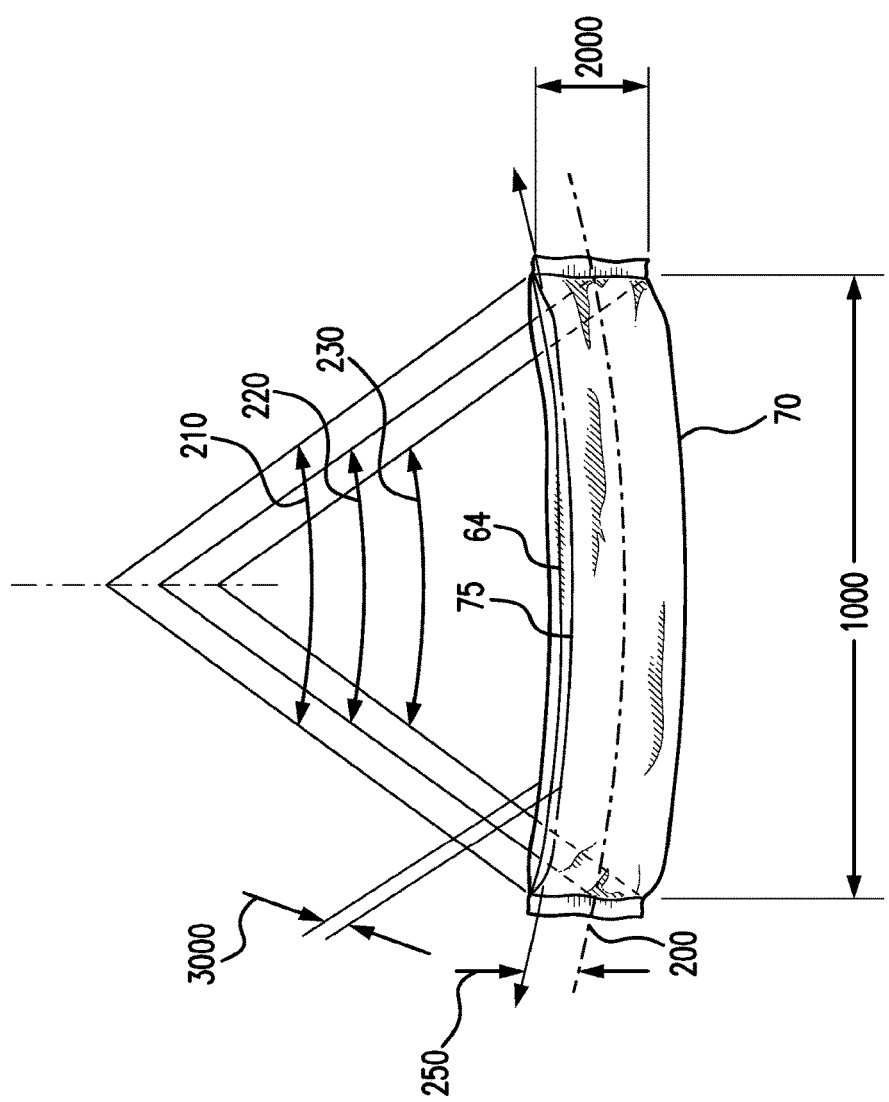
FIG. 2C shows a pouch having a gingival curve.

FIG. 2C shows a pouch having a gingival curve. FIG. 2C show examples of measurements of a gingival curves parallel to or along the length of the pouch 1. An angle of arc 210 can be measured parallel to or along the lower upper edge 75. An angle of arc 220 can be measured parallel to or along the gingival curve 200. An angle of arc 230 can be measured parallel to or along the first upper edge 70. The gingival curve 200 can have a curve depth 250. The curve depth 250 can be in a range of from for non-limiting example, zero to 5 cm, such as 1 mm, 2 mm, 3 mm, 4 mm, 5 mm, 10 mm, or greater.

FIG. 2C also shows a pouch length 1000, a pouch width 2000 and a pouch height 3000.

A gingival curve can be used along a pouch length 1000. A gingival curve can be used along a pouch width 2000. Thus, one or more portions of the pouch 1 can be curved to provide accommodation to and be configured with the shape of a user's gum, cheek and mouth. Thus, the topography of the pouch can be designed for the mouth comfort of and mouth fit to the user.

Figure 3:
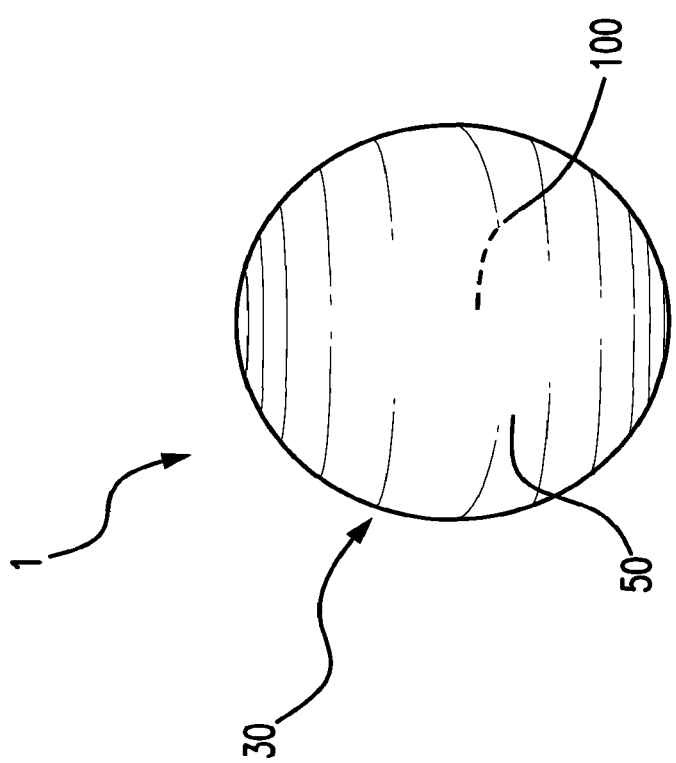
FIG. 3 is a three-dimensional view of a round (also herein as "spherical") pouch.

FIG. 3 is a three-dimensional view of a round pouch 30 (also as spherical pouch 30). FIG. 3 is a three-dimensional view of a round pouch. The pouch is spherical in shape and the contents of the pouch are held within the sphere. The spherical pouch is sealed, either by means of an overlapping flap which adheres to the surface of the spherical pouch or by means of a sealed opening, prior to which the spherical pouch is filled. The design of the pouch is intended to either be small enough to fit, with other spherical pouches between the cheek and gum or lip and gum, or in its larger iteration, it will mimic the playful shape of the gumball, fireball, gob stopper, or jawbreaker hard candies.

Figure 4:
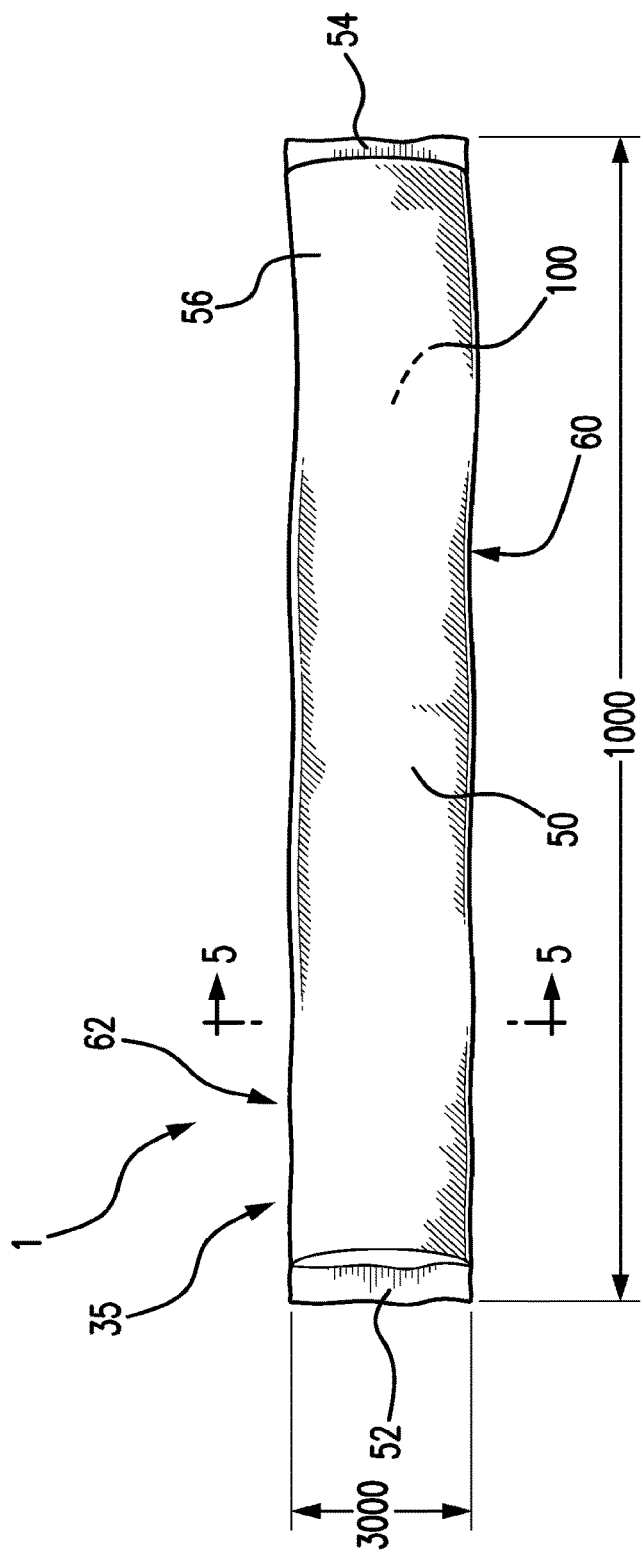
FIG. 4 is a two-dimensional view of cross-section of a tube-shaped pouch.

FIG. 4 is a two-dimensional view of cross-section of tube-shaped pouch having the tea composition contained in the pouch cavity 100. FIG. 4 is a two-dimensional view of cross-section of tube-shaped pouch. FIG. 4 is a two-dimensional view of a cross-section of the tube-shaped pouch. Each end of the pouch is sealed and the contents of the pouch are contained within the tubular shape of the pouch between the two sealed ends. The pouch is tube-shaped to offer comfort in that is has no sharp edges and its round, long shape fits comfortably between cheek and gum or lip and gum. The tubular shape is malleable when moist and can bend gently along the curve of mouth or jaw.

The example of FIG. 4, shows the side of the tube-shaped pouch. Each end of the pouch is sealed and the contents of the pouch are contained within the tubular shape of the pouch between the two sealed ends. The pouch is tube-shaped to offer comfort in that is has no sharp edges and its round, long shape fits comfortably between cheek and gum or lip and gum. The tubular shape is malleable when moist and can bend gently along the curve of mouth or jaw.

Figure 5:
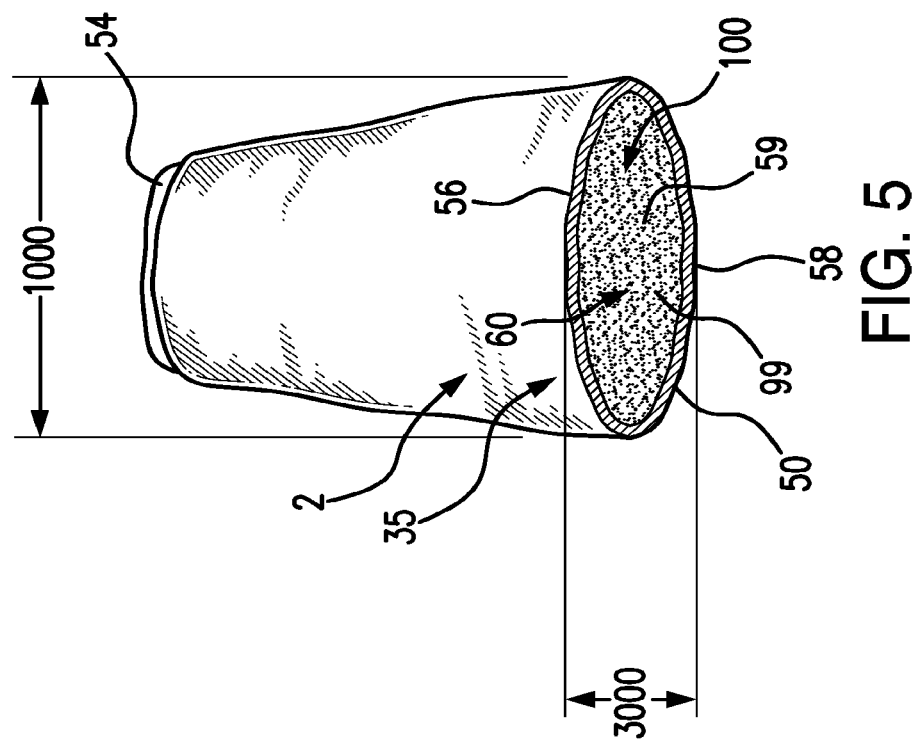
FIG. 5 is a cross sectional view of the tube-shaped pouch.

FIG. 5 is a cross sectional side view of the tube-shaped pouch 35. FIG. 5 is a cross-section taking along the height 3000 and length 1000 showing the tea composition 99 contained it the pouch cavity 100.

Figure 6:
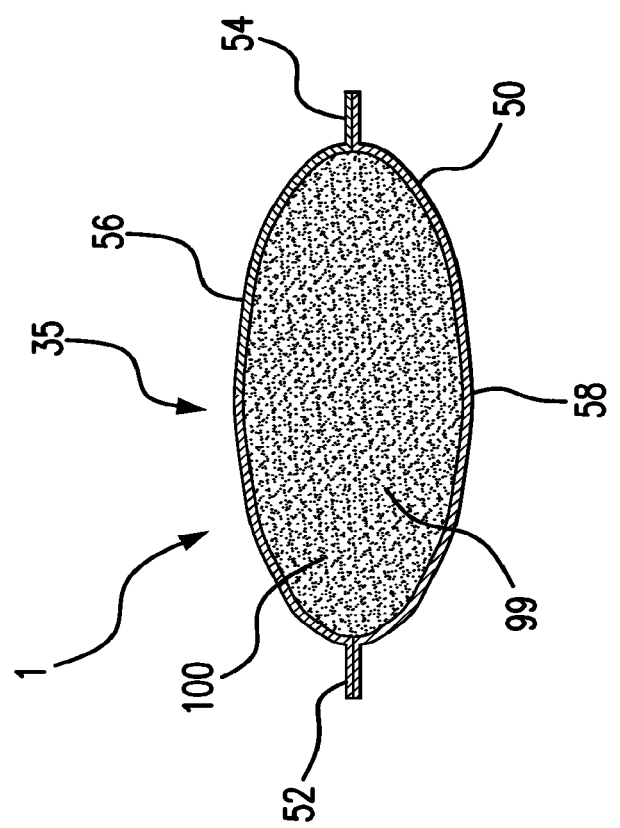
FIG. 6 is a view of a cross-section of square pouch.

FIG. 6 is a three-dimensional view of cross-section of square pouch showing the tea composition 99 contained it the pouch cavity 100.

FIG. 6 is a three-dimensional view of cross-section of square pouch. FIG. 6 is a three-dimensional view of a cross-section of the square pouch. Each end of the pouch is sealed and the contents of the pouch are contained within the hollow space between the two sealed ends and the two side walls of the pouch. The pouch is square with all four sides of equal length and the contents of the pouch are contained within the four sides of equal length and the two side walls of the pouch. The square pouch is smaller and more concentrated to take up less space in the mouth and be more inconspicuous to third parties. The smaller square shape also allows the pouch to be moved in the mouth more easily.

Figure 7:
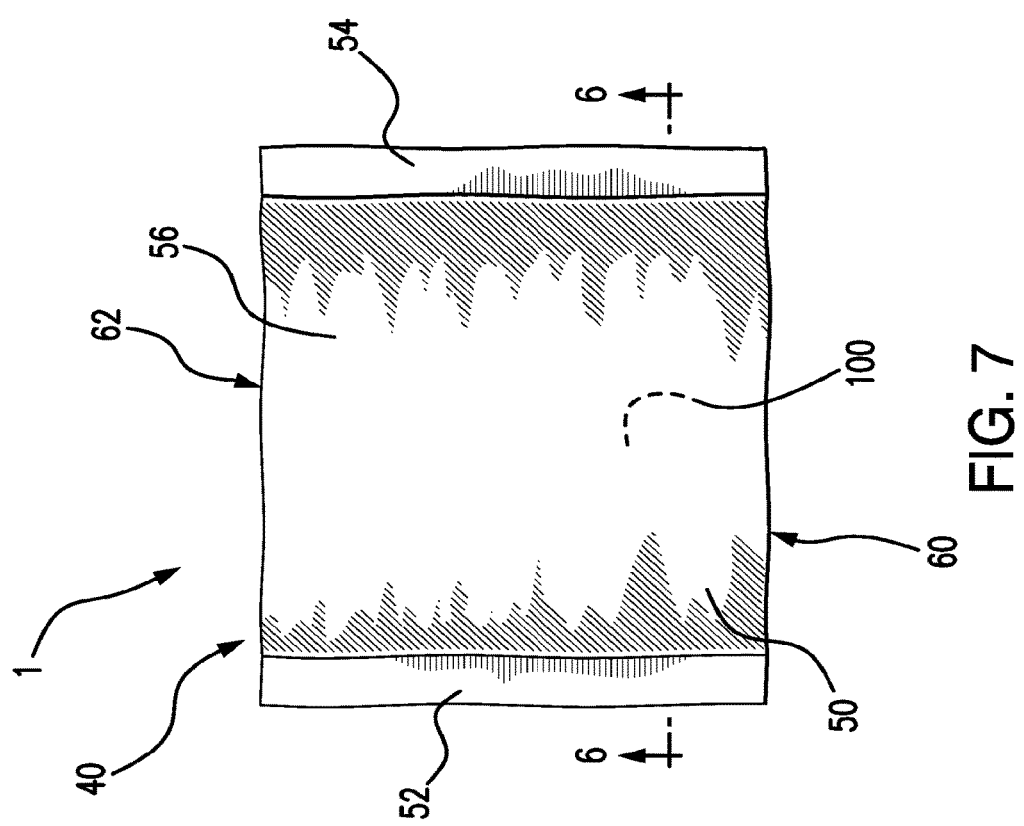
FIG. 7 is a two-dimensional side view of square pouch.

FIG. 7 is a two-dimensional side view of square pouch 40. FIG. 7 is a two-dimensional side view of the square pouch. Each end of the pouch is sealed and the contents of the pouch are contained within the hollow space between the two sealed ends and the two side walls of the pouch. The pouch is square with all four sides of equal length and the contents of the pouch are contained within the four sides of equal length and the two side walls of the pouch. The square pouch is smaller and more concentrated to take up less space in the mouth and be more inconspicuous to third parties. The smaller square shape also allows the pouch to be moved in the mouth more easily.

Figure 8:
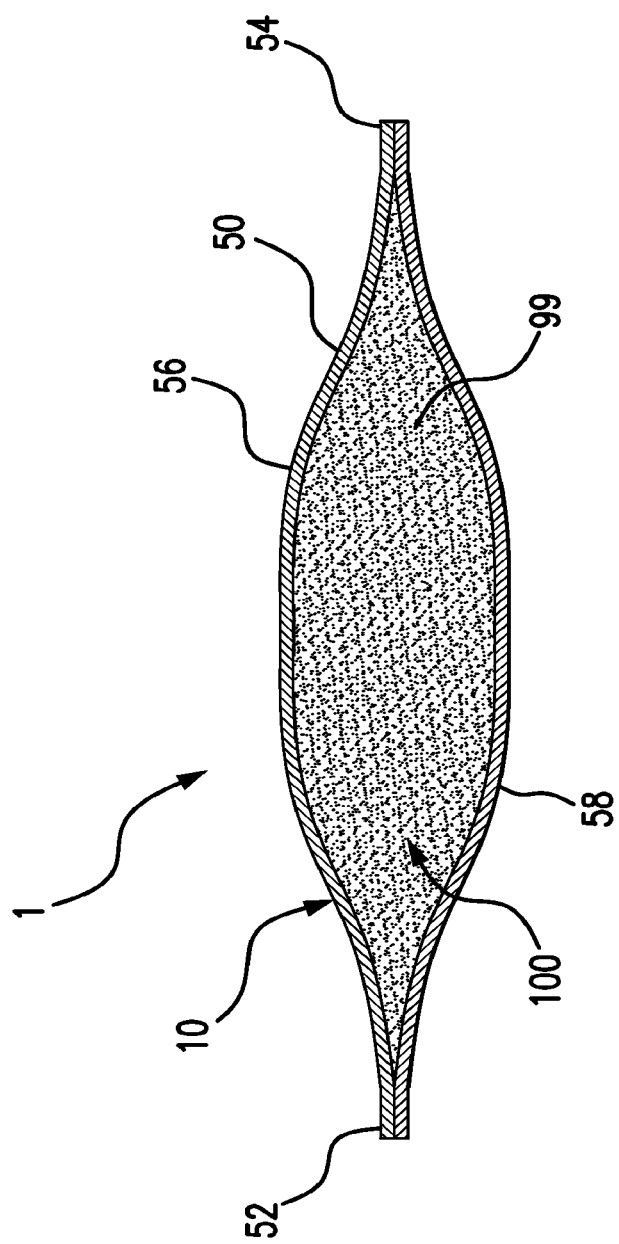
FIG. 8 is a view of cross-section of rectangle-shaped pouch.

FIG. 8 is a three-dimensional view of cross-section of rectangle-shaped pouch 10 (also as rectangular pouch 10). FIG. 8 is a three-dimensional view of a cross-section of the rectangle-shaped pouch. Each end of the pouch is sealed and the contents of the pouch are contained within the hollow rectangle space between the two sealed ends and the two side walls of the pouch. The pouch is rectangular with the top and bottom edges being longer than the two ends of the pouch. The rectangle shape of the pouch allows for a sizable space within the pouch and because it is longer than it is tall, it fits comfortably along the side of the mouth between cheek and gum or lip and gum. The rectangle shape allows the pouch to fit easily on either side of the mouth.

FIG. 9 is a two-dimensional side view of rectangle-shaped pouch 10 showing the tea composition 99 contained it the pouch cavity 100.

In an embodiment a surface of the pouch can have one or more of a coating. The one or more coatings can be used for flavor, texture, structure, hydrophilicity, hydrophobicity. The one or more coatings can be used to provide additives and/or flavorants.

In another embodiment the pouch can be infused with and/or can bear an additive and/or flavor in or on its structure. In an embodiment, the material of the pouch can bear deposited additives and/or flavorants.

For example, the pouch can be used as a carrier and/or carrying structure for additives and/or flavorants. In an embodiment, the pouch can bear a stimulant, a depressant, an additive and/or a flavor. For example, the pouch can be infused or bear caffeine, nicotine or other ingredient.

In an embodiment, the pouch can bear a mark, trademark watermark or other indicia. The material of the pouch can be chosen such that it can be marked and/or imprinted, or otherwise produced, to have and/or bear a marking, such as a word, design, trademark or other visibly recognizable feature to a user. In an embodiment, the indicia can be lettering or other text or design attribute.

In another embodiment, the pouch can be used for a flavor effect or to provide, change or modify a flavor profile.

FIG. 9 is a two-dimensional side view of rectangle-shaped pouch. FIG. 9 is a two-dimensional side view of a rectangle-shaped pouch. Each end of the pouch is sealed and the contents of the pouch are contained within the hollow rectangle space between the two sealed ends and the two side walls of the pouch. The pouch is rectangular with the top and bottom edges being longer than the two ends of the pouch. The rectangle shape of the pouch allows for a sizable space within the pouch and because it is longer than it is tall, it fits comfortably along the side of the mouth between cheek and gum or lip and gum. The rectangle shape allows the pouch to fit easily on either side of the mouth.

The scope of this disclosure is to be broadly construed. It is intended that this disclosure disclose equivalents, means, systems and methods to achieve the devices, activities and actions disclosed herein. For each formulation, element or constituent disclosed, it is intended that this disclosure also encompass in its disclosure and teaches equivalents, means, systems and methods for practicing the many aspects, mechanisms and devices disclosed herein. Additionally, this disclosure regards a tea for oral consumption and its many aspects, features and elements. Such a tea and the disclosed products, processes and mechanisms can be dynamic in their use and operation, this disclosure is intended to encompass the equivalents, means, systems and methods of the use of the tea, tea compositions, compositions, formulas and its many aspects consistent with the description and spirit of the operations and functions disclosed herein. The claims of this application are likewise to be broadly construed.

The description of the inventions herein in their many embodiments is merely exemplary in nature and, thus, variations that do not depart from the gist of the invention are intended to be within the scope of the invention. Such variations are not to be regarded as a departure from the spirit and scope of the invention.

The following claims are provided herein in order to promote a more clear understanding of certain embodiments of the invention, and are in no way intended as a limitation thereon.

We claim:

1. A preserved green tea composition consisting essentially of green tea leaf, green tea powder, yerba mate leaf, peppermint leaf, a peppermint leaf powder, honey powder, *stevia*, monk fruit, water and caffeine,
   wherein the composition is free of nicotine, and
   wherein the composition is free of tobacco.

2. A preserved green tea composition consisting essentially of green tea leaf, green tea powder, yerba mate leaf, peppermint leaf, a peppermint leaf powder, honey powder, *stevia*, monk fruit, sodium gluconate, water and caffeine,
   wherein the composition is free of nicotine, and
   wherein the composition is free of tobacco.

3. A preserved green tea composition consisting essentially of green tea leaf, green tea powder, yerba mate leaf, peppermint leaf, a peppermint leaf powder, honey powder, *stevia*, monk fruit, a tetrahydrocannabinol extract, sodium gluconate, water and caffeine,
   wherein the composition is free of nicotine, and
   wherein the composition is free of tobacco.

4. A preserved green tea composition consisting essentially of green tea leaf, green tea powder, yerba mate leaf, peppermint leaf, a peppermint leaf powder, honey powder, *stevia*, monk fruit, a cannabidiol, sodium gluconate, water and caffeine,
   wherein the composition is free of nicotine, and
   wherein the composition is free of tobacco.

* * * * *